(12) United States Patent
Brekan et al.

(10) Patent No.: US 9,481,850 B2
(45) Date of Patent: *Nov. 1, 2016

(54) MALEINIZED ESTER DERIVATIVES

(71) Applicant: Elevance Renewable Sciences, Inc., Woodridge, IL (US)

(72) Inventors: Jonathan Brekan, Chicago, IL (US); Stephen A. Di Biase, Chicago, IL (US); Zhe Wang, Aurora, IL (US); Amy Dalby, Woodstock, IL (US); Paul Bertin, Chicago, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/004,528

(22) Filed: Jan. 22, 2016

(65) Prior Publication Data

US 2016/0215233 A1    Jul. 28, 2016

Related U.S. Application Data

(63) Continuation of application No. 14/202,337, filed on Mar. 10, 2014, now abandoned.

(60) Provisional application No. 61/776,952, filed on Mar. 12, 2013.

(51) Int. Cl.
*C10M 169/04* (2006.01)
*C07C 69/34* (2006.01)
*C07D 307/34* (2006.01)
(Continued)

(52) U.S. Cl.
CPC .......... *C10M 169/04* (2013.01); *C07C 69/604* (2013.01); *C10M 105/04* (2013.01); *C10M 129/78* (2013.01); *C10M 159/12* (2013.01); *C10M 2205/0285* (2013.01); *C10M 2207/021* (2013.01); *C10M 2207/123* (2013.01); *C10M 2207/281* (2013.01); *C10M 2215/064* (2013.01); *C10N 2220/022* (2013.01); *C10N 2220/10* (2013.01); *C10N 2230/04* (2013.01); *C10N 2230/06* (2013.01); *C10N 2240/042* (2013.01); *C10N 2240/08* (2013.01); *C10N 2240/10* (2013.01); *C10N 2240/102* (2013.01);
(Continued)

(58) Field of Classification Search
None
See application file for complete search history.

(56) References Cited

U.S. PATENT DOCUMENTS

| | | | |
|---|---|---|---|
| 2,188,887 | A | 1/1940 | Clocker |
| 2,510,915 | A | 6/1950 | Spurlin et al. |

(Continued)

FOREIGN PATENT DOCUMENTS

| | | |
|---|---|---|
| DE | 188909 | 4/1906 |
| DE | 57961 | 9/1967 |

(Continued)

OTHER PUBLICATIONS

Hartel et al, Fette, Seifen, Anstrichmittel, vol. 88(8), pp. 300-303 (1984).

(Continued)

*Primary Examiner* — Vishal Vasisth
(74) *Attorney, Agent, or Firm* — Robert S. Dailey

(57) ABSTRACT

This disclosed invention relates to a maleinated ester derivative derived from an unsaturated linear aliphatic carboxylic acid methyl ester, maleic anhydride, and a monohydric alcohol. Lubricants and functional fluids containing the maleinated esters are disclosed.

17 Claims, 5 Drawing Sheets

(51) Int. Cl.

| | | |
|---|---|---|
| C07D 407/00 | (2006.01) | |
| C10M 159/12 | (2006.01) | |
| C10M 129/78 | (2006.01) | |
| C07C 69/604 | (2006.01) | |
| C10M 105/04 | (2006.01) | |

(52) U.S. Cl.
CPC ..... C10N2240/103 (2013.01); C10N 2240/40 (2013.01); C10N 2250/10 (2013.01)

(56) References Cited

U.S. PATENT DOCUMENTS

| | | |
|---|---|---|
| 2,569,420 A | 9/1951 | Kosmin et al. |
| 2,964,545 A | 12/1960 | Harrison |
| 3,293,201 A | 12/1966 | Shahade et al. |
| 3,776,866 A | 12/1973 | Nakayama |
| 4,376,068 A | 3/1983 | Mookherjee et al. |
| 4,390,444 A | 6/1983 | Mookherjee et al. |
| 4,446,125 A | 5/1984 | Mookherjee et al. |
| 4,505,934 A | 3/1985 | Gut et al. |
| 4,518,757 A | 5/1985 | Schulz et al. |
| 4,545,939 A | 10/1985 | Sekiguchi et al. |
| 4,690,767 A | 9/1987 | DiBiase |
| 5,425,789 A | 6/1995 | Lewtas et al. |
| 5,484,542 A | 1/1996 | Cahoon et al. |
| 5,730,029 A | 3/1998 | Stoldt et al. |
| 5,773,391 A | 6/1998 | Lawate et al. |
| 5,814,110 A | 9/1998 | Bartz et al. |
| 6,224,642 B1 | 5/2001 | Daly et al. |
| 6,458,175 B1 | 10/2002 | Lehmann et al. |
| 6,503,285 B1 | 1/2003 | Murphy |
| 6,645,261 B2 | 11/2003 | Murphy et al. |
| 6,727,357 B2 | 4/2004 | Polovsky et al. |
| 6,770,104 B2 | 8/2004 | Murphy |
| 6,773,469 B2 | 8/2004 | Murphy |
| 6,797,020 B2 | 9/2004 | Murphy |
| 7,022,637 B2 | 4/2006 | Song et al. |
| 7,128,766 B2 | 10/2006 | Murphy et al. |
| 7,192,457 B2 | 3/2007 | Murphy et al. |
| 7,217,301 B2 | 5/2007 | Murphy et al. |
| 7,247,742 B2 | 7/2007 | McMahon et al. |
| 7,309,817 B2 | 12/2007 | Green et al. |
| 7,399,323 B2 | 7/2008 | Renninger et al. |
| 7,462,205 B2 | 12/2008 | Murphy |
| 7,465,835 B2 | 12/2008 | Zones et al. |
| 7,473,284 B2 | 1/2009 | Krull |
| 7,476,264 B2 | 1/2009 | Krull |
| 7,494,961 B2 | 2/2009 | Small et al. |
| 7,531,082 B2 | 5/2009 | Mukherjee et al. |
| 7,592,295 B1 | 9/2009 | Fisher et al. |
| 7,637,968 B2 | 12/2009 | Murphy |
| 7,655,739 B1 | 2/2010 | McPhee et al. |
| 7,659,097 B2 | 2/2010 | Renninger et al. |
| 7,691,792 B1 | 4/2010 | Fisher et al. |
| 7,759,444 B1 | 7/2010 | McPhee |
| 7,812,185 B2 | 10/2010 | Burdett et al. |
| 7,833,294 B2 | 11/2010 | Murphy et al. |
| 7,846,222 B2 | 12/2010 | Renninger et al. |
| 7,854,774 B2 | 12/2010 | Renninger et al. |
| 7,868,114 B1 | 1/2011 | McPhee |
| 7,868,115 B1 | 1/2011 | McPhee |
| 2003/0136046 A1 | 7/2003 | Jackson et al. |
| 2004/0198614 A1 | 10/2004 | Calder |
| 2005/0154221 A1 | 7/2005 | Lysenko et al. |
| 2007/0039237 A1 | 2/2007 | Murphy et al. |
| 2007/0227400 A1 | 10/2007 | Zullo et al. |
| 2007/0270621 A1 | 11/2007 | Millis et al. |
| 2007/0282000 A1 | 12/2007 | Murphy et al. |
| 2008/0027194 A1 | 1/2008 | Schrodi |
| 2008/0033026 A1 | 2/2008 | Zullo et al. |
| 2008/0064891 A1 | 3/2008 | Lee |
| 2008/0119377 A1 | 5/2008 | Devlin et al. |
| 2008/0141580 A1 | 6/2008 | Tack |
| 2008/0194443 A1 | 8/2008 | Stohr et al. |
| 2009/0005610 A1 | 1/2009 | Hassan et al. |
| 2009/0048459 A1 | 2/2009 | Tupy et al. |
| 2009/0065736 A1 | 3/2009 | Johnson |
| 2009/0119977 A1 | 5/2009 | Murphy |
| 2009/0126602 A1 | 5/2009 | Murphy et al. |
| 2009/0137014 A1 | 5/2009 | Tsuruta et al. |
| 2009/0217568 A1 | 9/2009 | Murphy et al. |
| 2009/0220443 A1 | 9/2009 | Braksmayer et al. |
| 2009/0259065 A1 | 10/2009 | Abraham et al. |
| 2009/0264672 A1 | 10/2009 | Abraham et al. |
| 2010/0024281 A1 | 2/2010 | Lemke et al. |
| 2010/0047499 A1 | 2/2010 | Braksmayer et al. |
| 2010/0056714 A1 | 3/2010 | McPhee |
| 2010/0056743 A1 | 3/2010 | McPhee |
| 2010/0094034 A1 | 4/2010 | Kaido et al. |
| 2010/0112672 A1 | 5/2010 | Keasling et al. |
| 2010/0132250 A1 | 6/2010 | Uptain et al. |
| 2010/0145086 A1 | 6/2010 | Schrodi et al. |
| 2010/0160506 A1 | 6/2010 | Wu et al. |
| 2010/0190671 A1 | 7/2010 | Stoehr et al. |
| 2010/0191008 A1 | 7/2010 | Olson |
| 2010/0267971 A1 | 10/2010 | Ohler et al. |
| 2011/0015436 A1 | 1/2011 | Aoki et al. |
| 2011/0287989 A1 | 11/2011 | Filippini |
| 2012/0245063 A1 | 9/2012 | DiBiase et al. |
| 2012/0264664 A1* | 10/2012 | DiBiase .......... C08F 20/14 508/186 |

FOREIGN PATENT DOCUMENTS

| | | |
|---|---|---|
| EP | 0130753 | 9/1985 |
| EP | 0079906 | 1/1987 |
| EP | 0266822 | 5/1991 |
| EP | 0531842 | 3/1993 |
| EP | 0656414 | 6/1995 |
| EP | 1681338 | 7/2006 |
| FR | 2757535 | 6/1998 |
| GB | 824066 | 11/1959 |
| GB | 1215075 | 12/1970 |
| IT | 91MI0462 | 8/1992 |
| JP | S51-2705 | 6/1974 |
| JP | 512705 | 1/1976 |
| JP | 5849332 | 3/1983 |
| JP | (S)61-060793 | 3/1986 |
| JP | (H)8-208537 | 8/1996 |
| WO | WO 97/11098 | 3/1997 |
| WO | WO 02/086031 | 10/2002 |
| WO | WO 2004/101634 | 11/2004 |
| WO | WO 2004/113403 | 12/2004 |
| WO | WO 2005/071050 | 8/2005 |
| WO | WO 2007/140339 | 12/2007 |
| WO | WO 2008/008420 | 1/2008 |
| WO | WO 2008/039499 | 4/2008 |
| WO | WO 2008/045555 | 4/2008 |
| WO | WO 2008/124390 | 10/2008 |
| WO | WO 2009/003052 | 12/2008 |
| WO | WO 2009/006527 | 1/2009 |
| WO | WO 2009/067384 | 5/2009 |
| WO | WO 2009/080489 | 7/2009 |
| WO | WO 2009/113711 | 9/2009 |
| WO | WO 2010/027463 | 3/2010 |
| WO | WO 2010/027464 | 3/2010 |
| WO | WO 2010/033183 | 3/2010 |
| WO | WO 2010/042208 | 4/2010 |
| WO | WO 2010/051293 | 5/2010 |
| WO | WO 2010/074738 | 7/2010 |
| WO | WO 2010/103223 | 9/2010 |
| WO | WO 2010/115097 | 10/2010 |
| WO | WO 2011/002831 | 1/2011 |
| WO | WO 2011/022317 | 2/2011 |
| WO | WO 2011/031659 | 3/2011 |
| WO | WO 2011/034829 | 3/2011 |
| WO | WO 2011/037585 | 3/2011 |
| WO | WO 2011/038331 | 3/2011 |
| WO | WO 2011/149789 | 12/2011 |

OTHER PUBLICATIONS

Intl Preliminary Report on Patentability, PCT App. No. PCT/US2014/022954, dated Sep. 15, 2015.

(56) References Cited

OTHER PUBLICATIONS

Li et al., Chem. Phys. Lipids, vol. 158(1), p. 39 (2009).
Singh et al., J. Surfactants Detergents, vol. 9(2), pp. 191-195 (2006).
Samuelsson et al., J. Polymer Sci. Part A Polymer, vol. 42(24), pp. 6346-6352 (2004).
Dean et al., Accts. Chem. Res., vol. 40(10), p. 931 (2007) (abstract).
Trost et al., Tetrahedron Lett., vol. 40(44), pp. 7739-7743 (1999).
Zheng et al., Org. Lett., vol. 13(24), pp. 6448-6451 (2011).
Yang et al., Org. Lett., vol. 5(20), pp. 3749-3752 (2003).
Aminova et al., Deposited Doc., VINITI 732-735 (1975) (abstract).
Meng et al., Comunicaciones presentadas a la Jordanas del Comite Espanol de la Detergencia, vol. 31, pp. 299-312 (2001).
Swann, Jr., et al., Univ. Of Ill. Bull., vol. XXVII, No. 31, pp. 1-16 (1930).
U.S. Appl. No. 13/081,588, filed Apr. 7, 2011.
U.S. Appl. No. 13/281,108, filed Oct. 25, 2011.
U.S. Appl. No. 13/428,458, filed Mar. 23, 2012.
U.S. Appl. No. 13/428,257, filed Mar. 23, 2012.
U.S. Appl. No. 13/428,284, filed Mar. 23, 2012.
U.S. Appl. No. 13/428,268, filed Mar 23, 2012.
U.S. Appl. No. 13/407,850, filed Feb. 29, 2012.
Int'l App. No. PCT/US2012/030823, filed Mar. 28, 2012.
Int'l App. No. PCT/US2011/057713, filed Oct. 25, 2011.
Int'l App. No. PCT/US2012/030316, filed Mar. 23, 2012.
Int'l App. No. PCT/US2012/030282, filed Mar. 23, 2012.
Int'l App. No. PCT/US2012/030296, filed Mar. 23, 2012.
Int'l App. No. PCT/US2012/030291, filed Mar. 23, 2012.
Dorinson, ASLE Trans., vol. 14, pp. 124-134 (1971).
Holser et al., Fuel, vol. 85, pp. 393-395 (2006).
Tamayo et al., Anales de la Real Sociedad Espanola de Frisica y Quimica, Serie B, vol. 51 (1955).
Quesada et al., J. Am. Oil Chem. Soc., vol. 80(3), pp. 281-286 (2003).
Refvik et al., J. Am. Oil Chem. Soc., vol. 76(1), pp. 99-102 (1999).
Ross et al., J. Am. Chem. Soc., vol. 68(7), pp. 1373-1376 (1946).
Rybak et al., Eu. J. Lipid Sci. Tech., vol. 110, pp. 797-804 (2008).
Warwel et al., Indus. Crops Prods., vol. 20, pp. 301-309 (2004).
Warwel et al., Macromol. Chem. Phys., vol. 202, pp. 849-855 (2001).
Wang et al., Bioorg. Med. Chem., vol. 16, pp. 8413-8418 (2008).
Wu et al., J. Am. Oil Chem. Soc., vol. 77(5), pp. 561-563 (2000).
Int'l Search Report & Written Opinion, Int'l App. No. PCT/US2012/030823, dated Sep. 24, 2012.
Int'l Search Report & Written Opinion, Int'l App. No. PCT/US2011/057713, dated Mar. 14, 2012.
Int'l Search Report & Written Opinion, Int'l App. No. PCT/US2012/030316, dated Sep. 24, 2012.
Int'l Search Report & Written Opinion, Int'l App. No. PCT/US2012/030282, dated Aug. 27, 2012.
Int'l Search Report & Written Opinion, Int'l App. No. PCT/US2012/030296, dated Sep. 24, 2012.
Int'l Search Report & Written Opinion, Int'l App. No. PCT/US2012/030291, dated Sep. 24, 2012.
Vogel et al., Acct. Chem. Res., vol. 40(10), pp. 931-942 (2007).
Solov'ev et al., Izvestiya Vysshikh Uchebnykh Zavedenii i Khimicheskaya Tekhnologuya, vol. 49(9), pp. 121-123 (2003) (abstract).
Int'l Search Report & Written Opinion, Int'l App. No. PCT/US2014/022954, dated Jun. 27, 2014.

\* cited by examiner

| | | |
|---|---|---|
| 1 | = | Compressed Air |
| 2 | = | Air Manifold with Flow-meters |
| 3 | = | ~5 N KOH Pre-Trap |
| 4 | = | ABC Reagent Water Pre-Trap |
| 5 | = | Test Carboy |
| 6 | = | Insulated Magnetic Stir Plate |
| 7 | = | 0.2 N KOH Testing Traps |
| 8 | = | One-way Check Valves |

MALEINIZED ESTER DERIVATIVES

The present application is a continuation of U.S. patent application Ser. No. 14/202,337, filed Mar. 10, 2014, which claims the benefit of priority of U.S. Provisional Application No. 61/776,952 filed Mar. 12, 2013. This provisional application is incorporated herein by reference.

TECHNICAL FIELD

This invention relates to maleinized ester derivatives and, more particularly, to maleinized ester derivatives derived from unsaturated linear aliphatic carboxylic acid methyl esters, maleic anhydride, and monohydric alcohols. The invention relates to lubricants and functional fluids containing the maleinized ester derivatives.

BACKGROUND

Synthetic lubricants may be used in passenger car motor oils, heavy-duty diesel engine oils, marine and railroad engine lubricants, automatic transmission fluids, hydraulic fluids, gear oils, and industrial lubricants, such as metalworking fluids and lubricating greases.

SUMMARY

The purpose of these synthetic lubricants is to provide improved friction and wear control, rapid dissipation of heat, and the dissolution of and/or facilitating the removal of service-related contaminants. Achieving a proper balance between various performance characteristics is an important consideration in selecting a synthetic lubricant for a particular application. For example, polyolefin based lubricants typically exhibit good low-temperature properties, high viscosity index, and excellent thermal stability, but poor solvency. As a result, these lubricants tend to be inadequate without the presence of additional polar base stock-containing components. Conversely, polar base stock-containing lubricants, such as those based on synthetic esters and vegetable oils, typically exhibit good solvency and high surface affinity. However, these lubricants tend to be inadequate with respect to resistance to wear. The problem, therefore, is to provide a synthetic lubricant that exhibits both good solvency and good resistance to wear reduction characteristics. This invention provides a solution to this problem.

This invention relates to a composition comprising a maleinized ester derivative made by the reaction of: (i) an unsaturated linear aliphatic carboxylic acid methyl ester comprising a linear hydrocarbon chain of about 8 to about 18 carbon atoms, or about 10 to about 14 carbon atoms, or about 12 carbon atoms; maleic anhydride; and a monohydric alcohol of 3 to about 12 carbon atoms, or 3 to about 10 carbon atoms, or 3 to about 8 carbon atoms, or about 5 to about 10 carbon atoms, or about 5 carbon atoms; wherein the maleinized ester derivative comprises at least two proximal ester groups and another ester group, the proximal ester groups and the another ester group containing straight chain alkyl groups of 3 to about 12 carbon atoms, or 3 to about 8 carbon atoms, or about 5 carbon atoms; the proximal ester groups being separated from the another ester group by at least about 8 carbon atoms, or at least about 9 carbon atoms, or at least about 10 carbon atoms.

When counting the number of carbon atoms separating two ester groups, the carbonyl atoms of each ester group are included. For example, two proximal ester groups formed on a maleic anhydride group are separated by two carbon atoms, but when including the carbonyl atoms of the ester group, the proximal ester groups are separated by four carbon atoms. Similarly, when counting the number of carbon atoms between a proximal ester group and the another ester group, the carbonyl atoms of each ester group are included.

The monohydric alcohol may be linear or branched. In an advantageous embodiment of the invention, the monohydric alcohol comprises one or more linear alcohols.

In any of the above-indicated embodiments, the unsaturated linear aliphatic carboxylic acid methyl ester is reacted with the maleic anhydride to form a maleinized unsaturated carboxylic acid methyl ester, and the maleinized unsaturated carboxylic acid methyl ester is reacted with the monohydric alcohol to form the maleinized ester derivative.

In any of the above-indicated embodiments, prior to the reaction with the monohydric alcohol, the maleinized carboxylic acid methyl ester comprises a methyl ester group and a maleic anhydride group, the reaction with the monohydric alcohol comprising an esterification reaction with the maleic anhydride group and a transesterification reaction with the methyl ester group.

In any of the above-indicated embodiments, prior to the reaction with the monohydric alcohol, the maleinized carboxylic acid methyl ester comprises a methyl ester group and two maleic anhydride groups, the reaction with the monohydric alcohol comprising an esterification reaction with the maleic anhydride groups and a transesterification reaction with the methyl ester group.

In any of the above-indicated embodiments, the maleinized ester derivative comprises a mono-triester.

In any of the above-indicated embodiments, the maleinized ester derivative comprises a mixture of a mono-triester and a di-triester.

In any of the above-indicated embodiments, the maleinized ester is biodegradable.

In any of the above-indicated embodiments, the maleinized ester derivative is biodegradable.

In any of the above-indicated embodiments, the maleinized ester derivative contains one or more carbon-carbon double bonds, the carbon-carbon double bonds being hydrogenated to form saturated carbon bonds.

In any of the above-indicated embodiments, the unsaturated linear aliphatic carboxylic acid methyl ester comprises methyl 8-nonenoate, methyl 9-decenoate, methyl 10-undecenoate, methyl 9-dodecenoate, methyl 9-octadecenoate, or a mixture of two or more thereof.

In any of the above-indicated embodiments, the monohydric alcohol comprises 1-propanol, 1-butanol, 1-pentanol, 1-hexanol, 1-heptanol, 1-octanol, 1-decanol, 1-undecanol, 1-dodecanol, 2-methyl butanol, 3-methyl butanol, a $C_{10}$ branched alcohol, or a mixture of two or more thereof.

In any of the above-indicated embodiments, the unsaturated linear aliphatic carboxylic acid methyl ester comprises methyl 9-dodecenoate and the monohydric alcohol comprises 1-pentanol.

In any of the above-indicated embodiments, the unsaturated linear aliphatic carboxylic acid methyl ester is derived from a natural product. The natural product may comprise vegetable oil, algae oil, fungus oil, animal oil, animal fat, sucrose, lactose, glucose, fructose, canola oil, rapeseed oil, coconut oil, corn oil, cottonseed oil, olive oil, palm oil, peanut oil, safflower oil, sesame oil, soybean oil, sunflower seed oil, tall oil, linseed oil, palm kernel oil, tung oil, jatropha oil, mustard oil, camellina oil, pennycress oil, castor oil, coriander oil, almond oil, wheat germ oil, bone oil, lard, tallow, poultry fat, algae oil, yellow grease, fish oil, sugar cane, sugar beet, corn syrup, or a mixture of two or more thereof.

These compositions may be useful as additives as well as base stocks for lubricant compositions and/or functional fluid compositions. Because these compositions may be derived from natural products, they may be classified as renewable materials. This technology may be referred to as "green" technology.

DETAILED DESCRIPTION

Figure 1:
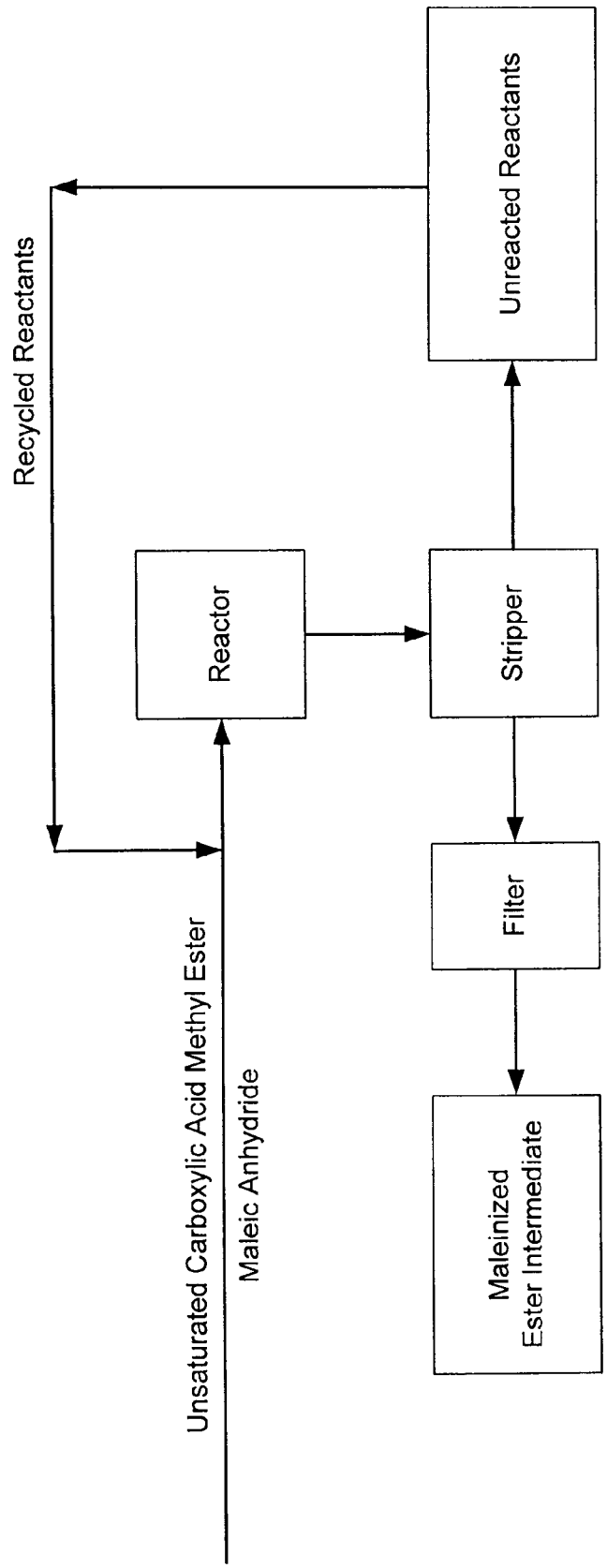
FIG. 1 is a flow sheet illustrating a process within the scope of the invention for reacting an unsaturated linear aliphatic carboxylic acid methyl ester with maleic anhydride to form a maleinized unsaturated carboxylic acid methyl ester. The maleinized unsaturated carboxylic acid methyl ester may be referred to as a maleinized ester intermediate.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "ester group" refers to a chemical group wherein a carbonyl is adjacent to an ether linkage. The ester group may be represented by the formula —COOR, wherein R is an alkyl group.

The term "proximal ester groups" refers to ester groups attached to the same compound and positioned within no more than about four carbon atoms from each other. The ester groups formed by the esterification of a maleic anhydride group may be referred to as proximal ester groups.

The term "another ester group" refers to an ester group attached to a compound that also contains two or more proximal ester groups, the another ester group not being one of the proximal ester groups.

The term "maleinized ester" refers to a product made by the reaction of an unsaturated carboxylic acid methyl ester with maleic anhydride. The maleinized ester may be referred to as a maleinized ester intermediate.

The term "maleinized ester derivative" refers to a product made by the reaction of a maleinized ester with a monohydric alcohol.

The term "unsaturated linear aliphatic carboxylic acid methyl ester" refers to a compound represented by the formula R—COOCH$_3$, wherein R is an unsaturated linear aliphatic hydrocarbon group (e.g., an alkenyl group). Examples of the unsaturated linear aliphatic carboxylic acid methyl esters that may be used include methyl 8-nonenoate, methyl 9-decenoate, methyl 10-undecenoate, methyl 9-dodecenoate, methyl 9-octadecenoate, or a mixture of two or more thereof.

The term "maleic anhydride" refers to a compound represented by the formula $C_2H_2(CO)_2O$. Maleic anhydride is the acid anhydride of maleic acid.

The term "monohydric alcohol" refers to a compound represented by the formula ROH, wherein R is a aliphatic hydrocarbon (e.g., alkyl) group. R may be branched or linear. In an advantageous embodiment, R is linear. Examples of the monohydric alcohols that may be used include 1-propanol, 1-butanol, 1-pentanol, 1-hexanol, 1-heptanol, 1-octanol, 1-decanol, 1-undecanol, 1-dodecanol, 2-methyl butanol, 3-methyl butanol, a $C_{10}$ branched alcohol, or a mixture of two or more thereof.

The term "natural product" is used herein to refer to products of nature, including natural oil, carbohydrates, and the like.

The term "natural oil" refers to oils or fats derived from plants or animals. The term "natural oil" includes natural oil derivatives, unless otherwise indicated, and such natural oil derivatives may include one or more natural oil derived unsaturated carboxylic acids or derivatives thereof. The natural oils may include vegetable oils, algae oils, fungus oils, animal oils or fats, tall oils, derivatives of these oils, combinations of two or more of these oils, and the like. The natural oils may include, for example, canola oil, rapeseed oil, coconut oil, corn oil, cottonseed oil, olive oil, palm oil, peanut oil, safflower oil, sesame oil, soybean oil, sunflower seed oil, linseed oil, palm kernel oil, tung oil, jatropha oil, mustard oil, camellina oil, pennycress oil, castor oil, coriander oil, almond oil, wheat germ oil, bone oil, lard, tallow, poultry fat, yellow grease, fish oil, mixtures of two or more thereof, and the like. The natural oil (e.g., soybean oil) may be refined, bleached and/or deodorized.

The natural product may comprise a refined, bleached and/or deodorized natural oil, for example, a refined, bleached, and/or deodorized soybean oil (i.e., RBD soybean oil). Soybean oil may comprises about 95% by weight or greater (e.g., 99% weight or greater) triglycerides of fatty acids. The fatty acids in the soybean oil may include saturated fatty acids, including palmitic acid (hexadecanoic acid) and stearic acid (octadecanoic acid), and unsaturated fatty acids, including oleic acid (9-octadecenoic acid), linoleic acid (9,12-octadecadienoic acid), and linolenic acid (9,12,15-octadecatrienoic acid).

The term "carbohydrate" is used herein to refer to a class of compounds with the empirical formula $C_m(H_2O)_n$ that comprise carbon, hydrogen and oxygen atoms, with a hydrogen:oxygen ratio of 2:1. An example is deoxyribose which has the empirical formula $C_5H_{10}O_4$. The carbohydrates include the saccharides. The saccharides may include: monosaccharides, disaccharides, oligosaccharides, and polysaccharides. The monosaccharides and disaccharides may be referred to as sugars. The sugars, which may be in the form of crystalline carbohydrates, may include sucrose, lactose, glucose, fructose, fruit sugar, and the like. These may be obtained from sugar cane, sugar beet, corn syrup, and the like.

The term "biodegradable" refers to a material that degrades to form $CO_2$ and water.

The term "metathesis reaction" refers to a catalytic reaction which involves the interchange of alkylidene units among compounds containing one or more carbon-carbon double bonds (e.g., olefinic compounds) via the formation and cleavage of the carbon-carbon double bonds. Metathesis may occur between two like molecules (often referred to as self-metathesis) and/or between two different molecules (often referred to as cross-metathesis).

The term "metathesis catalyst" refers to any catalyst or catalyst system that catalyzes a metathesis reaction.

Maleinized Ester

The maleinized ester may be formed by the reaction of an unsaturated linear aliphatic carboxylic acid methyl ester with maleic anhydride. The maleinized ester may be referred to as a maleinized ester intermediate. The maleinized ester derivative may be formed by reaction of the maleinized ester with a monohydric alcohol.

The unsaturated linear aliphatic carboxylic acid methyl ester may comprise an unsaturated linear aliphatic hydrocarbon chain (e.g., an alkenyl chain) of from about 8 to about 18 carbon atoms, or from about 10 to about 14 carbon atoms, or from about 10 to about 12 carbons, or about 12 carbon atoms, with one or more carbon-carbon double bonds in the hydrocarbon chain. The unsaturated linear aliphatic carboxylic acid methyl ester may be monounsaturated or polyunsaturated with, for example, from 1 to about 4, or 1 to about 3, or 1 or 2, or 1 carbon-carbon double bonds. When the hydrocarbon chain contains more than one carbon-carbon double bond, it may be partially hydrogenated to form a mono-unsaturated compound prior to being maleinized.

The unsaturated linear aliphatic carboxylic acid methyl ester may comprise methyl 8-nonenoate, methyl 9-decenoate, methyl 10-undecenoate, methyl 9-dodecenoate, methyl 9-octadecenoate, or a mixture of two or more thereof.

The unsaturated linear aliphatic carboxylic acid methyl ester may be derived from one or more natural products, including natural oil, carbohydrates, and the like. The unsaturated linear aliphatic carboxylic acid methyl ester may be derived from an estolide. The unsaturated linear aliphatic carboxylic acid methyl ester may be derived from a polyol ester, for example, a monoglyceride, diglyceride, triglyceride, or a mixture of two or more thereof.

The natural product may comprise one or more oils or fats derived from plants and/or animals. The natural oils may include vegetable oils, algae oils, fungus oils, animal oils or fats, tall oils, derivatives of these oils, combinations of two or more of these oils, and the like. The natural product may comprise one or more carbohydrates. The natural products may include sucrose, lactose, glucose, fructose, canola oil, rapeseed oil, coconut oil, corn oil, cottonseed oil, olive oil, palm oil, peanut oil, safflower oil, sesame oil, soybean oil, sunflower seed oil, linseed oil, palm kernel oil, tung oil, jatropha oil, mustard oil, camellina oil, pennycress oil, castor oil, tall oil, coriander oil, almond oil, wheat germ oil, bone oil, lard, tallow, poultry fat, yellow grease, fish oil, bone oil, mixtures of two or more thereof, and the like. The natural product may be a natural oil (e.g., soybean oil) which is refined, bleached and/or deodorized.

The natural product may comprise soybean oil. Soybean oil may comprise unsaturated glycerides, for example, in many embodiments about 95% weight or greater (e.g., 99% weight or greater) triglycerides. Major fatty acids making up soybean oil may include saturated fatty acids, palmitic acid (hexadecanoic acid) and stearic acid (octadecanoic acid), and unsaturated fatty acids, oleic acid (9-octadecenoic acid), linoleic acid (9,12-octadecadienoic acid), and linolenic acid (9,12,15-octadecatrienoic acid). Soybean oil may be a highly unsaturated vegetable oil with many of the triglyceride molecules having at least two unsaturated fatty acids. The soybean oil may be refined, bleached and/or deodorized.

The unsaturated linear aliphatic carboxylic acid methyl ester may be derived from a natural product using a metathesis reaction process. Metathesis is a catalytic reaction that involves an interchange of alkylidene units among compounds containing one or more carbon-carbon double bonds (i.e., olefinic compounds). The reaction mechanism involves cleavage and formation of carbon-carbon double bonds. Metathesis can occur between two of the same molecules (often referred to as self-metathesis) and/or it can occur between two different molecules (often referred to as cross-metathesis). The self-metathesis process may comprise reacting a natural product such as a natural oil or natural oil derived unsaturated carboxylic acid and/or ester in the presence of a metathesis catalyst to form a metathesized natural product.

The cross-metathesis process may comprise reacting a natural product such as a natural or natural oil derivative with another olefinic compound in the presence of a metathesis catalyst to form a product mixture containing the desired unsaturated carboxylic acid methyl ester. The another olefinic compound may be a natural product, natural oil, natural oil derivative or a short chain olefin. The short chain olefin may comprise an alpha olefin, an internal olefin, or a mixture thereof. The internal olefin may be symmetric or asymmetric. The olefin may comprise one or more of ethene, propene, 2-butene, 3-hexene, 4-octene, 2-pentene, 2-hexene, 2-heptene, 3-heptene, 2-octene, 3-octene, 2-nonene, 3-nonene, 4-nonene, ethylene, 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 1-eicosene, or a mixture of two or more thereof.

The catalyst used in the metathesis reaction may be any catalyst or catalyst system which catalyzes the metathesis reaction. The metathesis catalyst may be used, alone or in combination with one or more additional catalysts. Exemplary metathesis catalysts may include metal carbene catalysts based upon transition metals, for example, ruthenium, molybdenum, osmium, chromium, rhenium, and/or tungsten. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. 0859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

The product produced by the metathesis reaction may comprise one or more unsaturated carboxylic acids and/or esters. These may include glycerides and free fatty acids and/or esters. The acids and/or esters may be used as a source for the unsaturated carboxylic acid methyl esters of the present invention. In an embodiment, further processing may target, for example, $C_8$-$C_{18}$ fatty acid methyl esters. These may include methyl 8-nonenoate, methyl 9-decenoate, methyl 10-undecenoate, methyl 9-dodecenoate, methyl 9-octadecenoate, or a mixture of two or more thereof.

The natural product and/or natural product derived unsaturated carboxylic acid and/or ester may be partially hydrogenated prior to undergoing the metathesis reaction. Multiple unsaturated bonds within a polyunsaturated reactant provide multiple reaction sites. Multiple reaction sites may increase the chemical identity of the reaction products, which in turn may increase the complexity of the product composition. Multiple reaction sites within the reactants may also increase catalyst demand for the reaction. These factors may increase the overall complexity and inefficiency of the reaction process. More efficient reaction processes that can reduce catalyst demand and reduce complexity of the reaction product compositions may be provided by partially hydrogenating polyunsaturated reactants in the starting material prior to conducting the metathesis reaction process.

The unsaturated linear aliphatic carboxylic acid methyl esters may be partially hydrogenated prior to being reacted with the maleic anhydride to form the maleinized esters.

The hydrogenation reactions, as well as the metathesis reactions, and catalysts for such reactions, that may be used are described in more detail in U.S. patent publication 2012-0264664A1.

Figure 3:
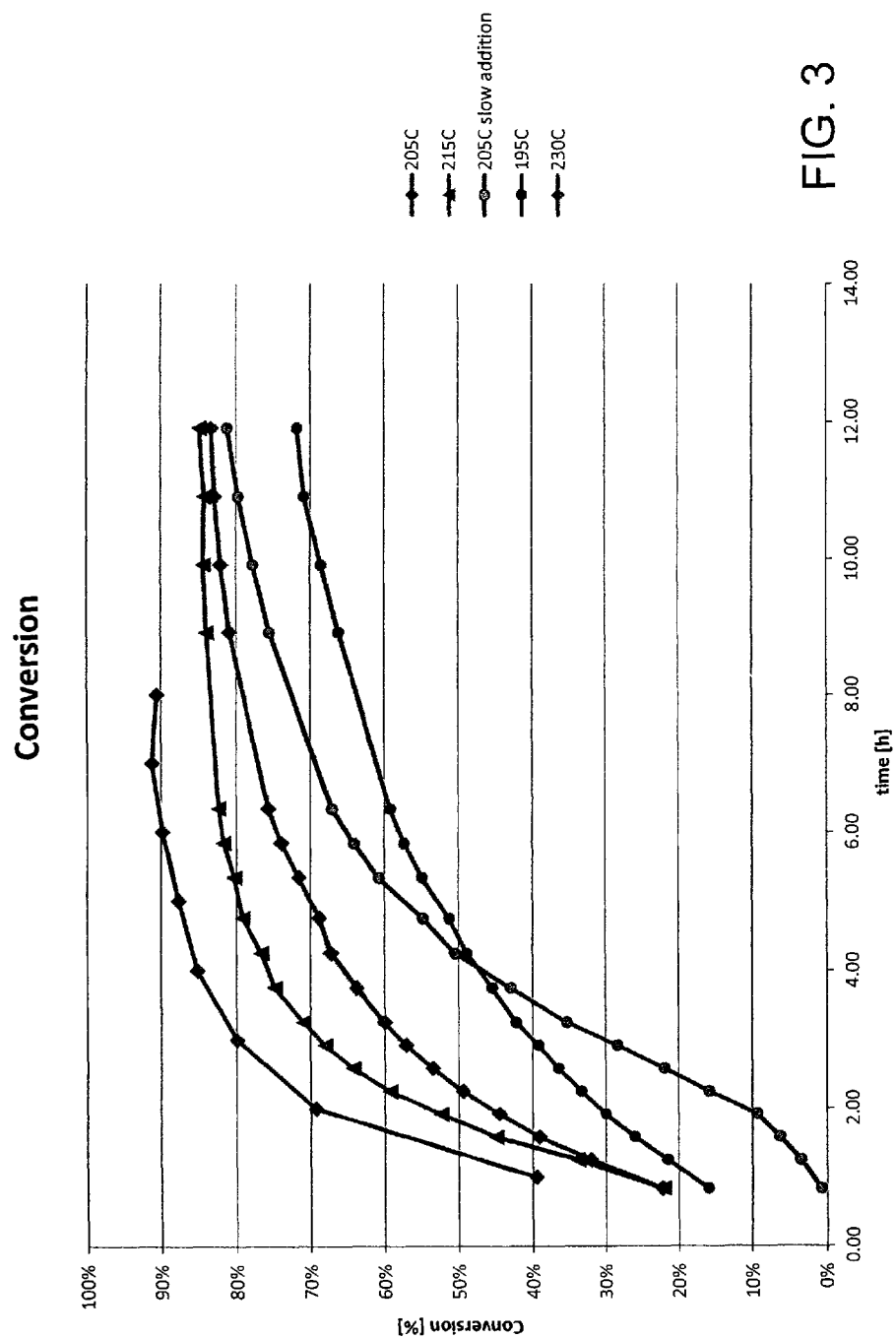
FIG. 3 is a chart showing conversions for the maleinization of methyl 9-dodecenoate at reaction temperatures of 195° C., 205° C., 215° C. and 230° C. over a reaction period of 12 hours.

The reaction between the unsaturated linear aliphatic carboxylic acid methyl ester and the maleic anhydride to form the maleinized ester may be a thermal reaction conducted without a catalyst, or it may be a catalytic reaction. The catalyst may comprise a dialkylperoxide, or a Lewis acid such as $AlCl_3$. The reaction temperature may be in the range from about 100° C. to about 300° C., or from about 150° C. to about 250° C., or from about 195° C. to about 240° C., or about 220° C. to about 240° C., or about 230° C. Lab studies for the maleinization of methyl 9-dodecenoate at reaction temperatures of 195° C., 205° C., 215° C. and 230° C. are shown in FIG. 3. A useful temperature for the maleinization of methyl 9-dodecenoate is 230° C. with a reaction time of 8 hours.

The molar ratio of equivalents of the unsaturated linear aliphatic carboxylic acid methyl ester to equivalents of the maleic anhydride may be from about 0.5:1 to about 4:1, or from about 1:1 to about 2:1. The weight of an equivalent of an unsaturated linear aliphatic carboxylic acid methyl ester as well as maleic anhydride is dependent on the number of carbon-carbon double bonds in the molecular structure of the compounds. For example, one mole of an unsaturated linear aliphatic carboxylic acid methyl ester having one carbon-carbon double bond in its molecular structure would have an equivalent weight equal to its molecular weight. Maleic anhydride, with one carbon-carbon double bond, has a equivalent weight equal to its molecular weight.

The amount of catalyst added to the reaction, when used, may be up to about 15 percent by weight of the unsaturated linear aliphatic carboxylic acid methyl ester, or from about 5 to about 15 percent by weight, or from about 5 to about 10 percent by weight.

The reaction may be conducted in an inert atmosphere, for example, a nitrogen atmosphere. The time of reaction may range from about 1 to about 24 hours, or from about 6 to about 18 hours, or from about 10 to about 16 hours, or about 8 hours.

Following the reaction, the product mixture may be subjected to isolation of the crude material. The crude material may be subjected to a vacuum to separate undesired volatile materials from the product which may be referred to as a maleinized ester.

The maleinized ester may comprise the product made by the reaction of maleic anhydride with an unsaturated linear aliphatic carboxylic acid methyl ester comprising methyl 8-nonenoate, methyl 9-decenoate, methyl 10-undecenoate, methyl 9-dodecenoate, methyl 9-octadecenoate, or a mixture of two or more thereof.

The maleinization of an unsaturated linear aliphatic carboxylic acid methyl ester to form a maleinized ester within the scope of the invention is shown below. The specific reaction that is shown is for the maleinization of methyl 9-dodecenoate. Some di-maleinization of the mono-maleinized materials may occur by the addition of a second maleic anhydride molecule to the mono-maleinized material. This reaction may produce about 3-5 wt % of the di-maleinized material in the reaction mixture. Isomers for the ene reaction that are believed to form are shown, however the 9,10 di-substitution may not occur for steric hindrance reasons and the isomer shown with a terminal double bond may be energetically unlikely.

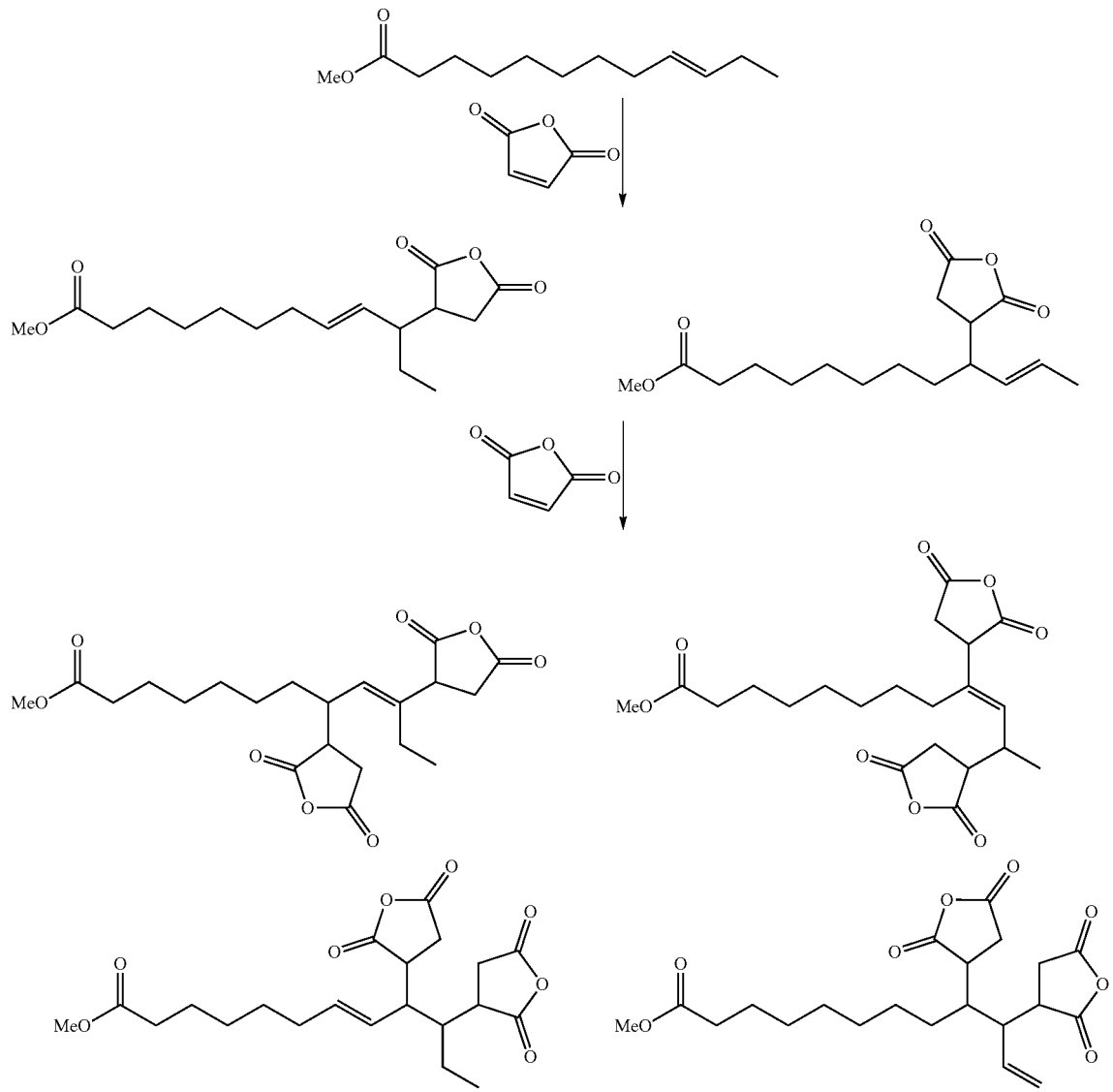

Maleinized Ester Derivative

The maleinized ester derivative of the invention may be made by reacting the above-indicated maleinized ester with a monohydric alcohol. The monohydric alcohol may be linear or branched. In an advantageous embodiment, the alcohol is linear. The monohydric alcohol may contain 3 to about 12 carbon atoms, or 3 to about 10 carbon atoms, or 3 to about 8 carbon atoms, or about 5 to about 10 carbon atoms, or about 5 carbon atoms. The monohydric alcohol may comprise 1-propanol, 1-butanol, 1-pentanol, 1-hexanol, 1-heptanol, 1-octanol, 1-decanol, 1-undecanol, 1-dodecanol, 2-methyl butanol, 3-methyl butanol, a $C_{10}$ branched alcohol, or a mixture of two or more thereof.

The ratio of C=O groups in the maleinized ester to —OH groups in the monohydric alcohol may be from about 1 to about 6, or from about 1 to about 3, or from about 1 to about 2, or about 1.

The reaction between the maleinized ester and the monohydric alcohol may be carried out in the presence of a catalyst. The catalyst may be a Lewis acid or a Broonsted acid. These may include one or more sulfonic acids. The catalyst may comprise methane sulfonic acid. The reaction may be enhanced by heating the reaction mixture to a temperature in the range from about 100° C. to about 250° C., or from about 100° C. to about 200° C., or from about 150° C. to about 200° C., or from about 160° C. to about 170° C.

The amount of catalyst added to the reaction may be from about 0.5 percent by weight to about 10 percent by weight of the maleinized ester, or from about 2 to about 4 percent by weight, or 3 percent by weight.

The reaction may be conducted in an inert atmosphere, for example, a nitrogen atmosphere. The time of reaction may range from about 4 to about 12 hours, or from about 6 to about 12 hours, or from about 8 to about 10 hours.

The reaction may be conducted at a pressure above atmospheric pressure, for example, in a stainless steel reactor with a back-pressure regulator. The internal pressure of the reaction may range from a gauge pressure of about 0 to about 60 psig (about 0 to about 414 kilopascals), or from about 30 to about 50 psig (about 207 to about 345 kilopascals), or about 45 psig (about 310 kilopascals).

The maleinized ester derivative formed by the reaction of the maleinized ester with the monohydric alcohol may comprise a triester. The triester may comprise a mono-triester, or a mixture of a mono-triester and a di-triester. The maleinized ester derivative can have up to three ester groups on the mono-maleinized molecules and up to five ester groups on the di-maleinized molecules.

The mechanism for the reaction of the maleinized ester with the monohydric alcohol may involve three reactions. The first reaction takes place with the anhydride ring opening and forming a half ester which includes an ester group and a free carboxylic acid group. The free carboxylic acid group then reacts with the alcohol and forms a diester. In addition, transesterification of the methyl ester group with the monohydric alcohol results in the formation of a triester. Representative structures for the reaction of maleinized methyl 9-dodecenoate and 1-pentanol are shown below.

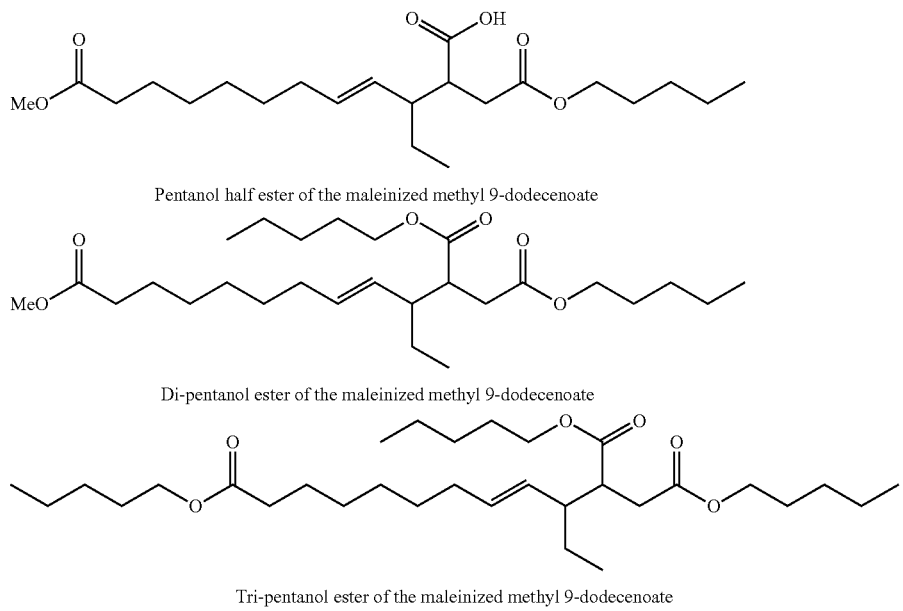

Pentanol half ester of the maleinized methyl 9-dodecenoate

Di-pentanol ester of the maleinized methyl 9-dodecenoate

Tri-pentanol ester of the maleinized methyl 9-dodecenoate

The initial ring opening reaction with the monohydric alcohol may produce no byproducts. The esterification of the carboxylic acid with the monohydric alcohol is a reversible reaction and produces water as a byproduct. The water is removed in order to shift the equilibrium to the ester and reduce the overall acidity of the product. The transesterification of the methyl ester with the monohydric alcohol produces methanol as a byproduct. This reaction is also reversible. The methanol is removed in order to drive the reaction towards the monohydric alcohol ester. The esterification and transesterification reactions may be driven to completion by using an excess of the monohydric alcohol and by removing the byproducts of reaction, water and methanol.

Figure 4:
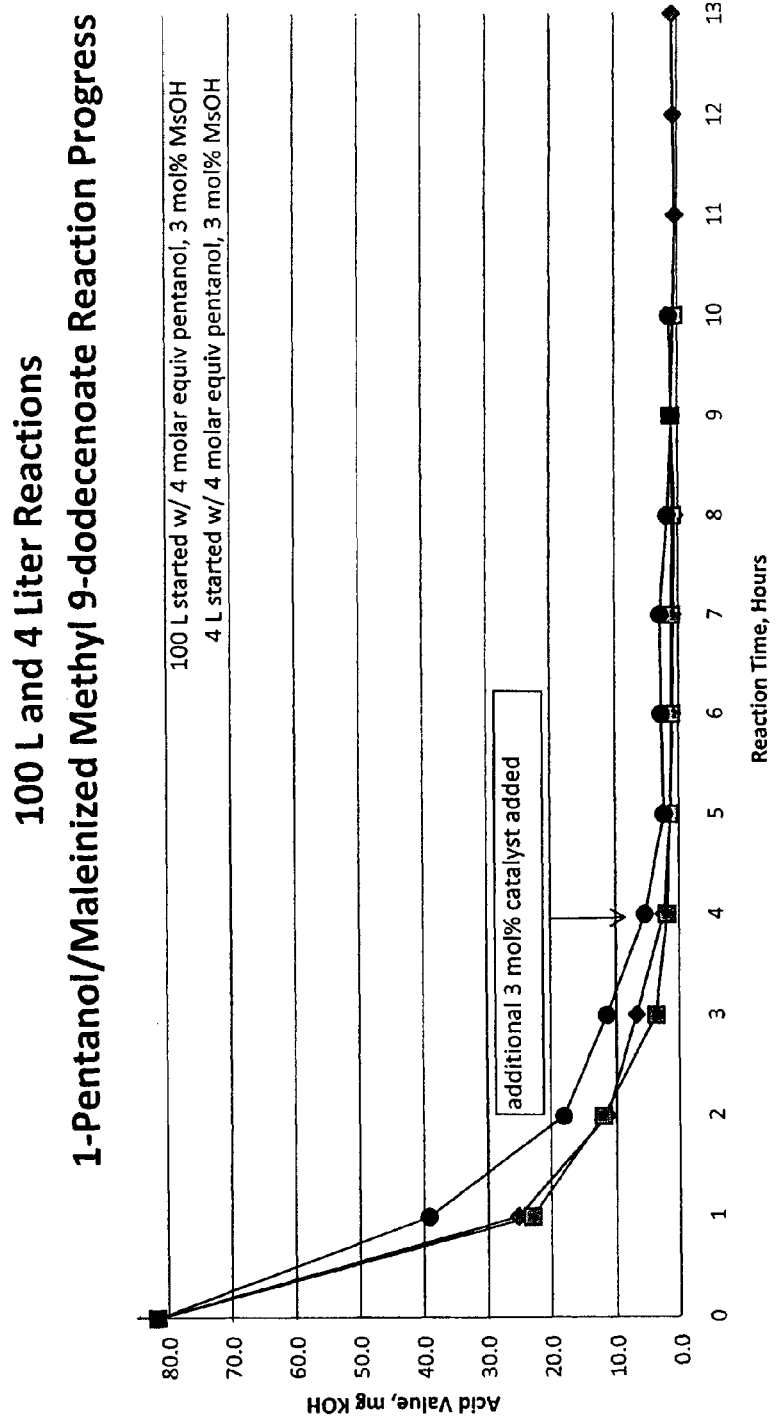
FIG. 4 is a chart showing acid value plots for reactions of maleinized methyl 9-dodecenoate with 1-pentanol.

The progress of the reaction may be monitored by measuring the acid value (AV) of the reaction mixture. For example, AV plots for the reaction of maleinized methyl 9-dodecenoate and 1-pentanol are shown in FIG. 4.

The maleinized ester derivatives formed by the reaction of maleinized esters with monohydric alcohols may be partially or fully hydrogenated to accommodate end use requirements. The hydrogenation process that may be used is described in U.S. patent publication 2012-0264664A1.

Lubricants and Functional Fluids

The lubricant and/or functional fluid compositions of the invention may comprise one or more of the above-identified maleinized ester derivatives. These derivatives may be useful as viscosity modifiers, solubility improvers, performance boosters, and the like, as well as base oils. These derivatives, when used as base oils, may be referred to as functional base oils. These derivatives may be blended with one or more conventional base oils.

The lubricant compositions may be effective as engine oil or crankcase lubricating oils for spark-ignited and compression-ignited internal combustion engines, including automobile and truck engines, two-stroke cycle engines, aviation piston engines, marine and diesel engines, stationary gas engines, and the like. The lubricant compositions may comprise engine oils. The functional fluids may comprise a driveline fluid such as an automatic transmission fluid, manual transmission fluid, transaxle lubricant, fluid for continuously variable transmissions, dual clutch automatic transmission fluid, farm tractor fluid, fluids for hybrid vehicle transmission, or gear oil. The functional fluid may comprise a metal-working lubricant, hydraulic fluid, or other lubricating oil or grease composition.

The maleinated ester derivatives may be biodegradable and may be used as functional base oils. The functional base oil may have a kinetic viscosity (ASTM D-445) in the range from about 2 to about 1000 cSt at 100° C., or from about 2 to about 500, or from about 2 to about 100, or from about 4 to about 10 cSt. The base oil may have a viscosity up to about 35 cSt at 100° C., or in the range from about 3 to about 35 cSt, or in the range from about 5 to about 35 cSt at 100° C.

The functional base oil may have a viscosity index (ASTM D2270) in the range from about 120 to about 250, or from about 130 to about 170.

The functional base oil may have a pour point (ASTM D97) in the range from about −20 to about −70° C., or from about −30 to about −45° C., or about −40° C.

The functional base oil may have an aniline point (ASTM D611) in the range from about 25 to about 120° C., or from about 50 to about 100° C.

The functional base oil may have oxidation induction time (ASTM D6186) at 210° C. in the range from about 1 to about 10 minutes, or from about 1 to about 3 minutes, or from about 5 to about 10 minutes.

The functional base oil may have an oxidation onset temperature (ASTM E2009) in the range from about 170° C. to about 220° C., or from about 190° C. to about 210° C.

The cold crank simulator viscosity test values (ASTM D5293) for the functional base oil may be in the range from about 13000 to about 9500 cP, or from about 7000 to about 9500 cP, at a temperature of −15° C.; or in the range from about 7000 to about 6600 cP, or from about 1000 to about 6200 cP, at a temperature of −35° C.

The evaporation loss (ASTM D5293) for the functional base oils may be in the range from about 5 to about 15%, or from about 4 to about 7%.

The functional base oils may exhibit enhanced values for high temperature shear stability, fuel economy, deposit control, oxidative stability, thermal stability, and the like.

The functional base oil may be used alone as the base oil or may be blended with an American Petroleum Institute (API) Group I, II, III, IV or V base oil, a natural oil, an estolide fluid, or a mixture of two or more thereof. Examples of the natural oil may include soybean oil, rapeseed oil, and the like. The blended base oil may contain from about 1% to about 75%, or from about 5% to about 60% by weight of the maleinized ester derivative.

The API Group I-V base oils have the following characteristics:

| Base Oil Category | Sulfur (%) | | Saturates (%) | Viscosity Index |
|---|---|---|---|---|
| Group I | >0.03 | and/or | <90 | 80 to 120 |
| Group II | ≤0.03 | and | ≥90 | 80 to 120 |
| Group III | ≤0.03 | and | ≥90 | ≥120 |
| Group IV | | All polyalphaolefins (PAO) | | |
| Group V | | All others not included in Groups I, II, III, or IV | | |

The Group I-III base oils are mineral oils.

The base oil may be present in the lubricant or functional fluid composition at a concentration of greater than about 60% by weight based on the overall weight of the lubricant or functional fluid composition, or greater than about 65% by weight, or greater than about 70% by weight, or greater than about 75% by weight.

When the maleinated ester derivatives are blended with polyalphaolefins to make up the base oil, the maleinated ester derivatives may comprise from about 10% to about 80%, or from about 20% to about 60%, or about 30% by weight of the base oil.

The polyalphaolefins blended with the maleinated ester derivates to make up the functional base oil may comprise any API Group IV polyalphaolefin. These may include poly(1-hexene), poly(1-octene), poly(1-decene), mixtures of two or more thereof, and the like. The polyalphaolefin may comprise a PAO-4, PAO-8, PAO-12, PAO-20, or a mixture of two or more thereof. The term "PAO-4" refers to a polyalphaolefin with a kinematic viscosity at 100° C. of about 4 (typically about 3 to 5) mm²/s as determined by Test Method GB/T265. The term "PAO-8" refers to a polyalphaolefin with a kinematic viscosity at 100° C. of about 8 (typically about 7 to 9) mm²/s. The term "PAO-12" refers to a polyalphaolefin with a kinematic viscosity at 100° C. of about 12 (typically about 11 to 13) mm²/s. The term "PAO-20" refers to a polyalphaolefin with a kinematic viscosity at 100° C. of about 20 mm²/s.

The lubricant or functional fluid may further comprise one or more dispersants and/or detergents. The dispersant may be present in the lubricant or functional fluid composition at a concentration in the range from about 0.01 to about 20% by weight, or from about 0.1 to about 15% by weight based on the weight of the lubricant or functional fluid. The detergent may be present in the lubricant or functional fluid composition at a concentration in the range from about 0.01% by weight to about 50% by weight, or from about 1% by weight to about 30% by weight based on the weight of the lubricant or functional fluid composition. The detergent may be present in an amount suitable to provide a TBN (total base number) in the range from about 2 to about 100 to the lubricant composition, or from about 3 to about 50. TBN is the amount of acid (perchloric or hydrochloric) needed to neutralize all or part of a material's basicity, expressed as milligrams of KOH per gram of sample.

The detergent may include one or more overbased materials prepared by reacting an acidic material (typically an inorganic acid or lower carboxylic acid, such as carbon dioxide) with a mixture comprising an acidic organic compound, a reaction medium comprising at least one inert, organic solvent (mineral oil, naphtha, toluene, xylene, etc.) for said acidic organic material, a stoichiometric excess of a metal base, and a promoter such as a calcium chloride, acetic acid, phenol or alcohol. The acidic organic material may have a sufficient number of carbon atoms to provide a degree of solubility in oil. The metal may be zinc, sodium, calcium, barium, magnesium, or a mixture of two or more thereof. The metal ratio may be from an excess of 1 to about 40, or in the range from about 1.1 to about 40. These detergents may include overbased sulfonates, overbased phenates, mixtures thereof, and the like.

The dispersant that may be used may include any dispersant known in the art which may be suitable for the lubricant or functional fluid compositions of this invention. These may include:

(1) Reaction products of carboxylic acids (or derivatives thereof), with nitrogen containing compounds such as amines, hydroxy amines, organic hydroxy compounds such as phenols and alcohols, and/or basic inorganic materials. These may be referred to as carboxylic dispersants. These may include succinimide dispersants, such as polyisobutenylsuccinimide.

(2) Reaction products of relatively high molecular weight aliphatic or alicyclic halides with amines, for example, polyalkylene polyamines. These may be referred to as "amine dispersants."

(3) Reaction products of alkylphenols with aldehydes (e.g., formaldehyde) and amines (e.g., polyalkylene polyamines), which may be referred to as "Mannich dispersants."

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like.

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be referred to as "polymeric dispersants."

The lubricant or functional fluid composition may further comprise one or more additional functional additives, including, for example, one or more corrosion-inhibiting agents, oxidation-inhibiting agents, pour point depressing agents, extreme pressure (EP) agents, antiwear agents, viscosity index (VI) improvers, friction modifiers (e.g., fatty friction modifiers), hindered amine, phenolic and/or sulfurized inhibitors, antioxidants, metal cutting additives (e.g., sulfur chloride), antimicrobial additives, color stabilizers, viscosity modifiers (e.g., ethylene propylene diene (EPDM) viscosity modifiers), demulsifiers, seal swelling agents, anti-foam agents, mixtures of two or more thereof, and the like.

Extreme pressure (EP) agents and corrosion and oxidation-inhibiting agents which may be included in the lubricants and/or functional fluids of the invention, may include chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbyl and trihydrocarbyl phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctyl phosphorodithioate, barium di(heptylphenyl)phosphorodithioate, cadmium dinonyl phosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents and corrosion-oxidation inhibitors may also serve as anti-wear agents. Zinc dialkyl phosphorodithioates are examples of such multifunctional additives.

Pour point depressants may be used to improve low temperature properties of the oil-based compositions. Examples of useful pour point depressants may include polymethacrylates; polyacrylates; polyacrylamides; condensation products of haloparaffin waxes and aromatic compounds; vinyl carboxylate polymers; and terpolymers of dialkyl fumarates, vinyl esters of fatty acids, alkyl vinyl ethers, or mixtures of two or more thereof.

The viscosity modifiers may include one or more polyacrylates, polymethacrylates, polyolefins, and/or styrene-maleic ester copolymers.

Anti-foam agents may be used to reduce or prevent the formation of stable foam. The anti-foam agents may include silicones, organic polymers, and the like.

The lubricant or functional fluid may include one or more thickeners to provide the lubricant or functional fluid with a grease-like consistency. The thickener may comprise lithium hydroxide, lithium hydroxide monohydrate, or a mixture thereof. The thickener may comprise 9-decenoic acid diol.

The functional additives may be added directly to the lubricant or functional fluid composition. Alternatively, the additives may be diluted with a substantially inert, normally liquid organic diluent such as mineral oil, naphtha, benzene, toluene or xylene, to form an additive concentrate, which may then be added to the lubricant and/or functional fluid. The functional additives may include the maleinized ester derivatives of the invention. These concentrates may contain from about 0.1 to about 99%, or from about 10% to about 90% by weight, of one or more of the additives. The remainder of the concentrate may comprise the substantially inert normally liquid diluent.

The following examples are provided to illustrate the invention.

EXAMPLE 1

0.355 kg (4.03 mol) 1-pentanol is charged to a reaction flask that is equipped with a thermocouple, addition funnel, nitrogen inlet, magnetic stirrer, and short-path distillation bridge. The alcohol is heated to 110° C. and methanesulfonic acid (1.5 mL, 70% aqueous solution) is added. Maleinized methyl 9-dodecenoate (0.32 kg, AV=420 mg KOH/g) is added dropwise using the addition funnel. The term "AV" refers to acid value. A reaction occurs. A ternary mixture of water, methanol and pentanol is removed via distillation. After the addition of the methyl 9-dodecenoate is completed the resulting reaction mixture is heated to 120° C. for an additional hour. The AV is monitored to observe the reaction progress, which is about 20. The temperature is further increased to remove excess 1-pentanol and obtain an AV<2. The reaction mixture is allowed to cool to room temperature and vacuum (2 torr) is applied to remove residual water and alcohol. The temperature is stepwise increased to 160° C. to remove all volatiles. The remaining ester product is filtered over a bed of silica (1 inch (2.54 cm) fritted funnel) by applying vacuum. The filtration yields a golden to amber oil. The amount of desired product is 0.38 kg (71% yield). KV (100° C.)=5.0 cSt; KV (40° C.)=24.73 cSt; and viscosity index (VI)=128.

EXAMPLE 2

Maleinized methyl 9-dodecenoate (50 g, 0.16 mol), 1-decanol (90.2 g, 0.58 mol), p-toluenesulfonic acid (1.5 g, 0.008 mol) and 50 milliliters (ml) of toluene are added to a one-liter, three-necked round-bottom flask at 23° C. under an air atmosphere. The flask is fitted with a thermocouple temperature regulator with heating mantle, Dean-Stark trap with condenser, and a stopper with a nitrogen needle inlet. Nitrogen gas is passed through the needle inlet into the head space of the apparatus (flow rate=2.5 ft$^3$/hr (70.8 liters/hr)) for 10 minutes. The temperature is increased to 115° C. After 60 minutes, the temperature is increased to 120° C. After an additional 90 minutes, the temperature is increased to 130° C. Approximately 12.8 ml of distillate is collected in the Dean-Start trap. An aliquot of the reaction mixture is taken at 4 hours into the reaction and measured for AV=2.3 mg KOH/g. The reaction mixture is stirred for another 2.5 hours (total reaction time 6.5 hours). The heating source is removed and the reaction mixture is allowed to cool to ambient temperature. Ethyl acetate (200 ml) is used to wash the reaction mixture using a separatory funnel. The resulting organic layer is washed with a NaOH solution (0.97 g NaOH in 480 ml H$_2$O) followed by washing with a saturated NaCl solution three times. The resulting organic solution is concentrated by a rotorary evaporator (5 Torr, 60° C.) to remove ethyl acetate and excess alcohol. A triester product is separated from residual alcohol and water by vacuum distillation (2 Torr, 25° C. to 135° C.). The triester product is in the form of a clear dark amber oil. Analysis of the product indicates a mass of 112 g; a yield of 94%; KV (100° C.)=8.05 cSt; KV (40° C.)=44.4 cSt; and viscosity index (VI)=152.

EXAMPLE 3

Maleinized methyl 9-dodecenoate (100 g, 0.32 mol), 3-methylbutanol (125 g, 1.42 mol), p-toluenesulfonic acid (3 g, 0.015 mol) and 100 milliliters (ml) of toluene are added to a one-liter, three-necked round-bottom flask at 23° C. under an air atmosphere. The flask is fitted with a thermocouple temperature regulator with heating mantle, Dean-Stark trap with condenser, and a stopper with a nitrogen needle inlet. Nitrogen gas is passed through the needle inlet into the head space of the apparatus (flow rate=2.5 ft$^3$/hr (70.8 liters/hr)) for 10 minutes. The temperature is increased to 115° C. After 60 minutes, the temperature is increased to 120° C. After an additional 90 minutes, the temperature is increased to 130° C. Approximately 12.8 ml of distillate is collected in the Dean-Start trap. An aliquot of the reaction mixture is taken at 4 hours into the reaction and measured for AV with the result being a AV of 7.6. The reaction mixture is stirred for another 2.5 hours (total reaction time 6.5 hours). The heating source is removed and the reaction mixture is allowed to cool to ambient temperature. Ethyl acetate (200 ml) is used to wash the reaction mixture using a separatory funnel. The resulting organic layer is washed with a NaOH solution (0.97 g NaOH in 480 ml H$_2$O) followed by washing with a saturated NaCl solution three times. The resulting organic solution is concentrated by a rotorary evaporator (5 Torr, 60° C.) to remove ethyl acetate and excess alcohol. A triester product is separated from residual alcohol and water by vacuum distillation (2 Torr, 25° C. to 135° C.). The triester product is in the form of a clear dark amber oil. Analysis of the product indicates a mass of 147.9 g; a yield of 88%; KV (100° C.)=5.8 cSt; KV (40° C.)=33.5 cSt; and viscosity index (VI)=115.

EXAMPLE 4

0.741 kg (8.4 mol) 2-methylbutanol is charged to a reaction flask that is equipped with a thermocouple, addition funnel, nitrogen inlet, magnetic stirrer, and short-path distillation bridge. The alcohol is heated to 110° C. and methanesulfonic acid (3.0 mL, 70% aqueous solution) is added. Maleinized methyl 9-dodecenoate (0.8 kg, AV=420 mg KOH/g) is added dropwise using the addition funnel. A reaction occurs. A ternary mixture of water, methanol, and reactant alcohol is removed via distillation. After the addition is completed the resulting reaction mixture is heated to 120° C. for an additional hour. The AV is monitored to observe the reaction progress, which is about 20. The temperature is further increased to remove excess 2-methylbutanol and obtain an AV<2. The reaction mixture is allowed to cool to room temperature and vacuum (2 torr) is applied to remove residual water and alcohol. The temperature is stepwise increased to 160° C. to remove all volatiles. The remaining ester product is filtered over a bed of silica (1 inch (2.54 cm), fritted funnel) by applying vacuum. The filtration yields a golden to amber oil. The amount of desired product is 0.877 kg (65% yield). KV (100° C.)=5.99 cSt; KV (40° C.)=37.58 cSt; and viscosity index (VI)=102.

EXAMPLE 5

Maleinized methyl 9-dodecenoate (100 g, 0.32 mol), Exxal10 ((C$_{10}$ branched alcohol from ExxonMobil), 179.2 g, 1.13 mol), p-toluenesulfonic acid (3 g, 0.015 mol) and 100 milliliters (ml) of toluene are added to a one-liter, three-necked round-bottom flask at 23° C. under an air atmosphere. The flask is fitted with a thermocouple temperature regulator with heating mantle, Dean-Stark trap with condenser, and a stopper with a nitrogen needle inlet. Nitrogen gas is passed through the needle inlet into the head space of the apparatus (flow rate=2.5 ft$^3$/hr (70.8 liters/hr)) for 10 minutes. The temperature is increased to 115° C. After 60 minutes, the temperature is increased to 120° C. After an additional 90 minutes, the temperature is increased to 130° C. Approximately 12.8 ml of distillate is collected in the Dean-Start trap. An aliquot of the reaction mixture is taken at 4 hours into the reaction and measured for AV with the result being a TAN of 7.6. The reaction mixture is stirred for another 2.5 hours (total reaction time 6.5 hours). The heating source is removed and the reaction mixture is allowed to cool to ambient temperature. Ethyl acetate (200 ml) is used to wash the reaction mixture using a separatory funnel. The resulting organic layer is washed with a NaOH solution (0.97 g NaOH in 480 ml H$_2$O) followed by washing with a saturated NaCl solution three times. The resulting organic solution is concentrated by a rotorary evaporator (5 Torr, 60° C.) to remove ethyl acetate and excess alcohol. A triester product is separated from residual alcohol and water by vacuum distillation (2 Torr, 25° C. to 135° C.). The triester product is in the form of a clear dark amber oil. Analysis of the product indicates a mass of 149 g; a yield of 63%; KV (100° C.)=10.4 cSt; KV (40° C.)=79.9 cSt; and viscosity index (VI)=113.

Samples of products from Examples 1 to 5 are tested for viscosity index or VI (ASTM D2270) with the results indicated in Table 1.

TABLE 1

| Example | Alcohol | Viscosity Index |
|---|---|---|
| 1 | 1-Pentanol | 128 |
| 2 | 1-Decanol | 152 |
| 3 | 3-Methylbutanol | 115 |
| 4 | 2-Methylbutanol | 102 |
| 5 | Exxal 10 ($C_{10}$ branched alcohol) | 113 |

EXAMPLE 6

Maleinized methyl 9-dodecenoate is made by the reaction of methyl 9-dodecenoate and maleic anhydride via an "Ene" reaction. The maleinized methyl 9-dodecenoate is then reacted with 1-pentanol in the presence of methane sulfonic acid in an esterification/transesterification reaction to form a mixture of a mono-triester and a di-triester. The following reactants and catalyst are used:

| Name | CAS # |
|---|---|
| Methyl 9-dodecenoate | 39202-17-0 |
| Maleic anhydride | 108-31-6 |
| 1-Pentanol | 71-41-0 |
| Methanesulfonic acid | 75-75-2 |

Step 1:

The apparatus for conducting the maleinization reaction process includes a reactor, stripper and filter. A flow sheet for the process is shown in FIG. 1. A fresh feed containing methyl 9-dodecenoate and maleic anhydride is added to the reactor, heated to 75-90° C. and agitated to melt the maleic anhydride and mix it into the methyl 9-dodeconate. The reaction temperature is 220° C.-240° C. The pressure in the reactor is approximately 30 psig (206.8 kilopascals). The reaction mixture is stripped in the stripper at a temperature of 200° C. and a pressure of <2 Torr. The desired product, which is in the form of a maleinized ester intermediate, is separated from the unreacted reactants (and some intermediate), and filtered. The unreacted reactants are recycled to the reactor. A material balance for Step 1 of the process is as follows (all numerical values being in kilograms):

| | Fresh Feed | Recycle | Product |
|---|---|---|---|
| Methyl 9-dodecenoate | 519.7 | 168.2 | 8.4 |
| Maleic anhydride | 256.3 | 120 | — |
| Mono-maleinized methyl 9-dodecenoate | — | 28.9 | 730 |
| Di-maleinized methyl 9-dodecenoate | — | — | 35.6 |

Figure 2:
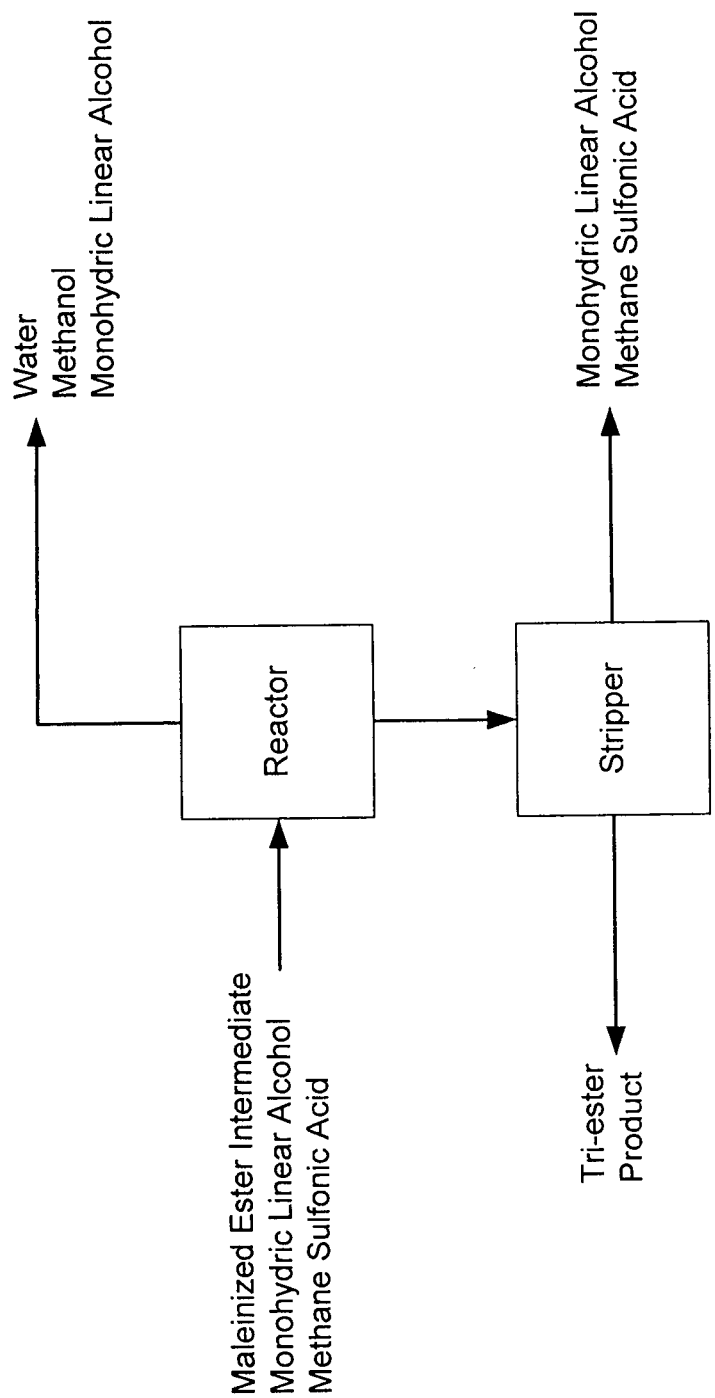
FIG. 2 is a flow sheet illustrating a process within the scope of the invention for esterifying a maleinized unsaturated carboxylic acid methyl ester (or maleinized ester intermediate).

Step 2:

The esterification reaction process is conducted using the process illustrated in FIG. 2. The apparatus for conducting the esterification process includes a reactor and a stripper. The reactor is setup with an overhead system able to collect 5-10 liters of overhead condensate. The process includes three separate reactions, namely, an anhydride ring opening reaction, an esterification reaction with the maleic anhydride group, and a transesterification reaction where the 1-pentanol replaces the methyl ester group. 1-Pentanol (31.0 Kg) and methanesulfonic acid (0.253 Kg) are loaded into the reactor and heated to 110° C. with agitation. The maleinized ester intermediate from Step 1 (27.3 Kg) is added over a 30 minute period. After the maleinized ester intermediate is added, the reactor is closed up and the nitrogen sparge is set at 140 ml/min. The internal pressure is controlled and regulated at 45 psig (310 kilopascals). The temperature of the reactor is increased to 160° C. After the reactor reaches 160° C., the pressure is slowly reduced until the overhead condensation rate is approximately 2 liters per minute. The pressure is continually decreased to meet the above overhead condensate flow rate. Every hour from time zero, reactor samples are taken to measure for AV. The pressure is continually decreased until it reaches 0 psig (0 kilopascals gauge pressure). At approximately, 3 hours the pressure is 0 psig (0 kilopascals) and TAN is equal to 5 mg KOH/g or below. An additional 6 L of pentanol and 0.253 Kg of methanesulfonic acid are added and the reaction pressure is increased to 20 psig (138 kilopascals) or adjusted to maintain an overhead flow rate of 2 L per minute. The pressure is decreased slowly to maintain that flow rate until the pressure is 0 psig (0 kilopascals). At this point the temperature is increased to 170° C. The reaction is terminated when the TAN is below 3 mg KOH/g. The reaction mixture is stripped at 175° C. and <2 to Torr to separate unreacted pentanol (268.9 Kg) and methanesulfonic acid (about 1 Kg) from the esterified product. The esterified product contains 41.5 Kg of a triester of the maleinized methyl 9-dodeconate.

The triester comprises a mixture of positional and olefin isomers. The major component (~95%), a mono-triester, of this material is comprised of a triester in isomeric form. Two proximal ester groups are separated from a third ester group by an unsaturated carbon chain of $C_{11}$ to $C_{14}$ in length. The proximal ester groups are separated by a $C_4$ saturated carbon chain. The minor component (~5%), a di-triester, comprises five ester groups, where four proximal esters are separated from the fifth ester groups by an unsaturated carbon chain of $C_{11}$ to $C_{16}$ in length. The alkyl portions of the ester groups have the structure $nC_5H_{12}$. These structures are shown below.

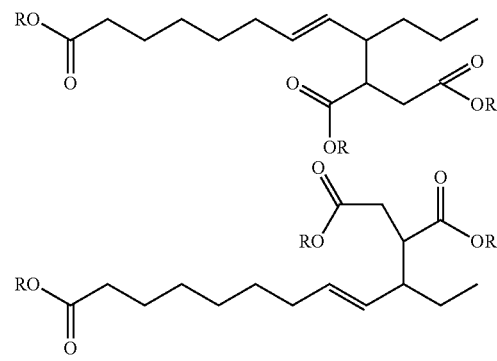

Mono-triester isomers, ~95%

-continued

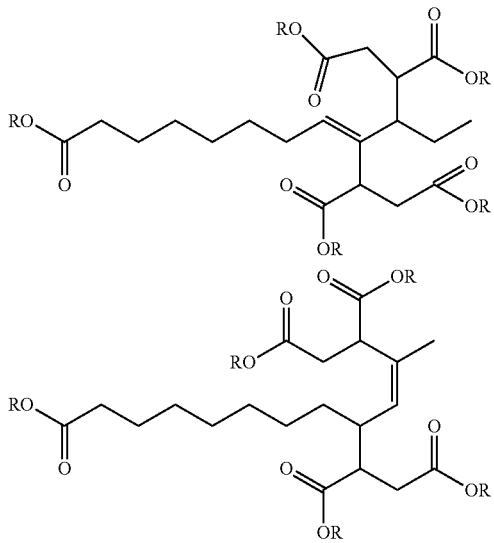

Di-triester isomers, ~5%

R = n-C$_5$H$_{12}$

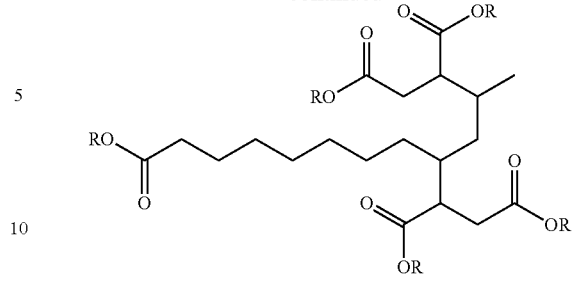

Di-triester isomers, ~5%

R = n-C$_5$H$_{12}$

EXAMPLE 7

The triester from Example 6 is subjected to a hydrogenation reaction using a transition metal, hydrogenation catalyst. The carbon-carbon double bonds are converted to saturated carbon bonds with the hydrogenation reaction. The resulting structures are shown below.

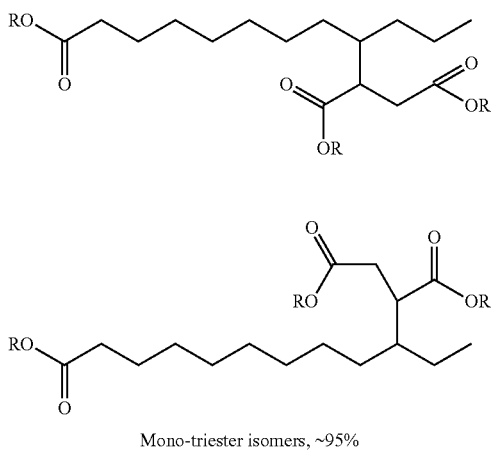

Mono-triester isomers, ~95%

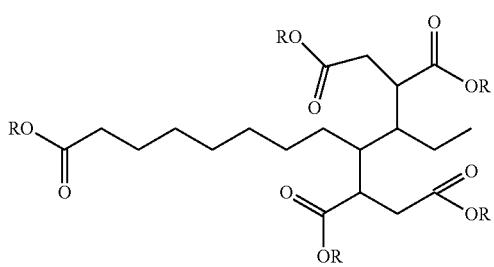

EXAMPLE 8

A triester derived from maleinized methyl 9-dodecenoate and 1-pentanol is blended with a polyalphaolefin base stock and an antioxidant to form a lubricating oil composition. This formulation is subjected to a Sequence IIIG Engine Test with the results showing improved average weighted piston deposit values. This indicates that fewer deposits are forming leading to a cleaner running engine. The lubricating oil formulation that is used is a SAE Viscosity 0W-20 oil which contains the following ingredients:

|  | Wt % |
| --- | --- |
| Triester derived from maleinized methyl 9-dodecenoate and 1-pentanol | 30.0 |
| PAO-4 polyalphaolefin | 69.5 |
| Irganox L57 (octylated/butylated diphenylamine antioxidant from Ciba Specialty Chemicals) | 0.5 |

The Sequence IIIG Test is an industry standard fired-engine, dynamometer lubricant test for evaluating automotive engine oils for certain high-temperature performance characteristics, including oil thickening, varnish deposition, oil consumption, and engine wear. Such oils include both single viscosity grade and multi-viscosity grade oils that are used in spark-ignition, gasoline-fueled engines, as well as diesel engines.

The Sequence IIIG Test utilizes a 1996 General Motors Powertrain 3800 Series II, water-cooled, 4 cycle, V-6 engine as the test apparatus. The Sequence IIIG test engine is an overhead valve design (OHV) and uses a single camshaft operating both intake and exhaust valves via pushrods and hydraulic valve lifters in a sliding-follower arrangement. The engine uses one intake and one exhaust valve per cylinder. Induction is handled by a modified GM port fuel injection system setting the air-to-fuel ratio at 15:1. The test engine is overhauled prior to each test, during which critical engine dimensions are measured and rated or measured parts (pistons, camshaft, valve lifters, etc.) are replaced.

The Sequence IIIG Test consists of a 10-minute operational check, followed by 100 hours of engine operation at moderately high speed, load, and temperature conditions. The 100-hour segment is broken down into five 20-hour test segments. Following the 10-minute operational check and each 20-hour segment, oil samples are drawn from the engine. The kinematic viscosities of the 20-hour segment samples are compared to the viscosity of the 10-minute sample to determine the viscosity increase of the test oil. The results are indicated below.

|  | Viscosity Increase (%) | Average Cam + Lifter Wear (μm) | Average Weighted Piston Deposits (merits) |
|---|---|---|---|
| Original Results | 69.51 | 51.4 | 5.46 |
| Transformed Results [B] | 4.241471 | 3.9396 |  |
| Industry Correction Factor | 0.000000 | 0.0000 | 0.0000 |
| Corrected Transformed | 4.241471 | 3.9396 |  |
| Severity Adjustment | −0.497540 | 0.3594 | 0.4102 |
| Final Transformed Result | 3.743931 | 4.2990 |  |
| Final Original Unit Result | 42.3 | 73.6 | 5.87 |
| Oil Consumption Hours, h [C] |  |  | 100 |
| Maximum Cam + Lifter Wear, μm |  |  | 69 |
| Average Oil Ring Plugging, % |  |  | 0 |
| Average Piston Varnish, merits |  |  | 9.70 |
| Oil Consumption, L |  |  | 2.71 |
| Number of Cold-Stuck Rings |  |  | 0 |
| Number of Hot-Stuck Rings |  |  | 0 |

[B] Viscosity Increase uses LN (PVIS), Average Cam + Lifter Wear uses LN (ACLW), Weighted Piston Deposits does not use a transformation
[C] Test hours at which Oil Consumption is calculated
[D] Non-Reference Oil Tests Only Viscosity Increase Data (cSt at 40° C.)

| Hours | Viscosity | Change | Percent |
|---|---|---|---|
| New Oil | 42.13 |  |  |
| Initial [B] | 40.97 |  |  |
| 20 | 44.18 | 3.21 | 7.84 |
| 40 | 46.77 | 5.80 | 14.16 |
| 60 | 49.94 | 8.97 | 21.89 |
| 80 | 54.14 | 13.17 | 32.15 |
| 100 | 69.45 | 28.48 | 69.51 |

Results of ICP Analysis of Used Oil [C]

| Hours | Iron | Copper | Lead |
|---|---|---|---|
| Initial | 8 | 2 | 2 |
| 20 | 61 | 30 | 31 |
| 40 | 118 | 35 | 36 |
| 60 | 172 | 34 | 38 |
| 80 | 250 | 39 | 43 |
| 100 | 357 | 43 | 68 |

[A] 8000 cSt is the Maximum Allowable Viscosity
[B] at the End of Leveling Run
[C] Units are in ppm (parts per million).

| Number | Camshaft Lobe, μm | Valve Lifter, μm | Cam and Lifter Wear, μm |
|---|---|---|---|
| 1 | 1 | 49 | 50 |
| 2 | 3 | 38 | 41 |
| 3 | 3 | 46 | 49 |
| 4 | 11 | 48 | 59 |
| 5 | 3 | 47 | 50 |
| 6 | 8 | 45 | 53 |
| 7 | 3 | 44 | 47 |
| 8 | 5 | 47 | 52 |
| 9 | 5 | 49 | 54 |
| 10 | 5 | 43 | 48 |
| 11 | 7 | 38 | 45 |
| 12 | 12 | 57 | 69 |
| Maximum | 12 | 57 | 69 |
| Minimum | 1 | 38 | 41 |
| Average | 6 | 46 | 51.4 |

| Piston | Oil Ring Land Deposit, Merits | % Chipped |
|---|---|---|
| 1 | 8.65 | 0 |
| 2 | 5.82 | 0 |
| 3 | 3.32 | 0 |
| 4 | 1.90 | 0 |
| 5 | 6.73 | 0 |
| 6 | 8.07 | 0 |
| Average | 5.75 | 0.00 |

| Piston | % Oil Ring Plugging | Ring Sticking [A] Hot-Stuck Rings | Ring Sticking [A] Cold Stuck Rings |
|---|---|---|---|
| 1 | 0 | N | N |
| 2 | 0 | N | N |
| 3 | 0 | N | N |
| 4 | 0 | N | N |
| 5 | 0 | N | N |
| 6 | 0 | N | N |
| Total |  | 0 | 0 |
| Average | 0 |  |  |

[A] Possible Values
T = Top Compression Ring
B = Bottom Compression Ring
O = Oil Ring
N = None

|  | Grooves, merits | | | Lands, merits | | Undercrown, |
|---|---|---|---|---|---|---|
|  | 1 | 2 | 3 | 2 | 3 | merits |
| Piston 1 | 3.89 | 7.27 | 9.45 | 5.62 | 8.66 | 2.82 |
| Piston 2 | 3.54 | 4.85 | 8.69 | 2.17 | 5.82 | 2.24 |
| Piston 3 | 4.37 | 1.03 | 9.02 | 0.99 | 3.32 | 1.67 |
| Piston 4 | 0.75 | 0.74 | 8.20 | 0.71 | 1.90 | 1.33 |
| Piston 5 | 0.75 | 3.73 | 8.93 | 0.85 | 6.73 | 1.94 |
| Piston 6 | 1.97 | 3.10 | 9.31 | 1.62 | 8.07 | 2.19 |
| WF | 0.05 | 0.10 | 0.20 | 0.15 | 0.30 | 0.10 |

Note:
These are Unweighted Ratings.

Piston Skirt Varnish, merits

|  | Thrust | Anti-Thrust | Average |
|---|---|---|---|
| Piston 1 | 9.95 | 10.00 | 9.98 |
| Piston 2 | 9.11 | 10.00 | 9.56 |
| Piston 3 | 9.71 | 9.91 | 9.81 |
| Piston 4 | 8.71 | 9.95 | 9.33 |
| Piston 5 | 9.57 | 9.90 | 9.74 |
| Piston 6 | 9.52 | 10.00 | 9.76 |
| Average | 9.43 | 9.96 | 9.70 |
| WF |  |  | 0.10 |

PSVAVx = (PSTx + PSVAx)2 Where x = Number of Piston
PSVTAV = Average of Six Thrust Piston Skirt Ratings
PSVAAV = Average of Six Anti-Thrust Piston Skirt Rating
APV = Average of All 12 Piston Ratings.

|  | Total Weighted Deposits, merits |
|---|---|
| Piston 1 | 7.53 |
| Piston 2 | 5.65 |
| Piston 3 | 4.42 |
| Piston 4 | 3.49 |
| Piston 5 | 5.51 |
| Piston 6 | 6.13 |

WPDX = (WF*G1Px) + (WF*G2Px) + WF*G3Px) = (WF*L2P) + (WF*ORLDx) = (WF*UCPx) + (WF*PSVAVx)
Where: x = Number of Piston
WF = Appropriate Weighting Factor (WF) for Part, From Table
Average Weighted Piston Deposits, merits  5.46

WPD = (WPD1 + WPD2 + WPD3 + WPD4 + WPD5 + WPD6)/6

EXAMPLE 9

A maleinized ester derivative in the form of hydrogenated 1-pentyl triester of maleinated-9-dodecene methyl ester (hereinafter the "test substance") is evaluated for aerobic biodegradability in water containing mineral salts and activated sludge. The activated sludge is taken from a wastewater treatment plant and is used as a source of microbial inoculum. The objectives of the study are: 1) to evaluate the biodegradability (mineralization to $CO_2$ production) potential of the test substance in an aerobic, aqueous medium; and 2) to determine the mineralization potential of a reference chemical in order to assess the viability of the test inoculum.

The test substance is in the form of a slight yellow oily liquid. It has the molecular formula $C_{32}H_{60}O_6$, and a carbon content of 71.07%.

The reference substance is sodium benzoate, CAS No. 532-32-1. The molecular formula is $C_6H_5COONa$. The chemical purity of the reference substance is 99.9%.

The reagent water is purified, deionized and filtered.

Approximately one liter of activated sludge is used as the microbial inoculum. The sludge is collected from the Columbia Wastewater Plant in Columbia, Mo. This plant treats predominately domestic sewage.

An aqueous mineral salts medium provides essential mineral nutrients and trace elements necessary to sustain the inoculum throughout the test period. The mineral salts medium is prepared by addition of reagent grade salts to reagent water. The mineral salts include salts of K, Na, $NH_4$, Ca, Mg and Fe. The pH of the mineral salts medium is 7.27.

Figure 5:
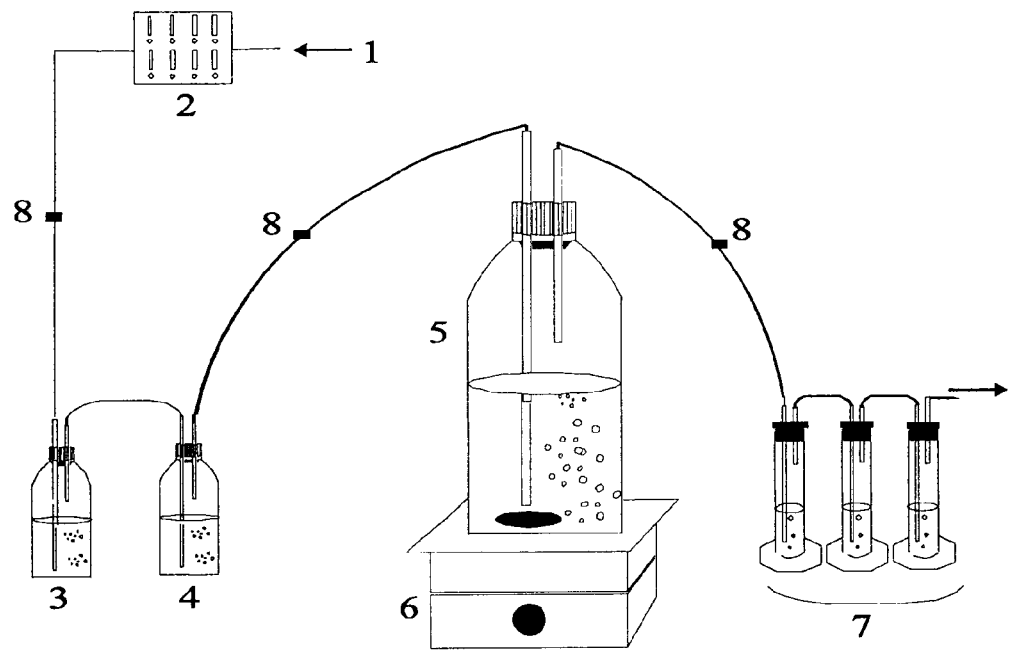
FIG. 5 is a schematic illustration of the test apparatus used in Example 9.

Each test system consists of a 5-L Pyrex carboy (reaction flask or vessel) containing a 3.0 L test solution volume comprised of mineral salts medium, prepared microbial inoculum, reagent water, and the appropriate test and/or reference substance additions. Outside air is passed through a pre-trap containing 500 mL of approximately 5 N KOH. The air is then passed through approximately 500 mL of reagent water to humidify the air, as well as to prevent contamination of the flasks from the KOH pre-trap. The $CO_2$-free and humidified air is then passed through the reaction flasks. This is shown in FIG. 5.

The $CO_2$-free air is introduced into each flask by positive pressure, and the flow rates (50-100 mL/minute) are measured and adjusted using flow meters. The outlet from each flask is connected to three $CO_2$ absorber gas-washing traps in series, each filled with 100 mL of 0.2 N KOH solution. These traps capture the $CO_2$ evolved from the reaction flasks. A magnetic stir bar is placed in each flask. The flasks are placed on insulated magnetic stir plates and stirred throughout the duration of the study. The test systems are kept in the dark (except for sampling and maintenance) in a temperature-controlled environmental chamber set at 22° C. Temperature of the chamber is continuously measured using a Rees Scientific temperature monitoring system.

The activated sludge is homogenized in a blender at a medium speed for two minutes. The homogenized sludge is allowed to settle for 30 to 60 minutes then filtered through glass wool. A volume of 30 mL of the filtrate is used as the inoculum for each reaction flask.

The suspended solids concentration in each filtered solution is determined by filtering three 10 mL aliquots of sludge through pre-weighed Whatman glass-fiber filter pads, followed by drying on a Mettler HR73P halogen moisture analyzer. The increase in weight of the filter pads is used to determine the suspended solids level. The suspended solids concentration of the prepared activated sludge is determined in the triplicate aliquots to be 0.4, 0.2, and 0.4 g/L, which corresponds to a mean of 0.3 g/L. The total concentration of suspended solids in each reaction flask (30 mL of inoculum to 3,000 mL of test medium) is 3 mg/L.

A 1.00-mg/mL stock solution of the reference substance is prepared by weighing 500.8 mg of sodium benzoate into a 500-mL Class A volumetric flask, correcting for purity (99.9%), and bringing the solution to volume with reagent water. The solution is stored refrigerated when not in use.

One day prior to dosing, six test systems are assembled. Each 5-L carboy receives 2,400 mL of mineral salts medium and 30 mL of the prepared activated sludge. Stirring and aeration with $CO_2$-free air at approximately 90 mL/minute is started for each flask. The flasks are allowed to aerate overnight to purge the systems of $CO_2$ before initiation of the test (dosing on Day 0).

Duplicate control systems are prepared by adding 570 mL of reagent water to the 5-L carboys. The final volume is 3,000 mL.

Duplicate test substance systems are prepared by adding 570 mL of reagent water and approximately 42.2 mg (dosed gravimetrically) of the test substance to two of the 5-L carboys. The nominal concentration of carbon from the test substance in the final volume of 3,000 mL of solution is 10 mg C/L.

The reference substance system is prepared by adding 467 mL of reagent water and 103 mL of the 1.00-mg/mL reference substance stock solution to a 5-L carboy. The nominal concentration of carbon from the reference substance in the final volume of 3,000 mL of solution is 20 mg C/L.

The toxicity control system is prepared by adding 467 mL of reagent water, 103 mL of the 1.00-mg/mL reference substance stock solution, and approximately 42.2 mg (dosed gravimetrically) of the test substance to a 5-L carboy. The nominal concentration of carbon from the toxicity system in the final volume of 3,000 mL of solution is 30 mg C/L.

After all additions, each of the reaction flasks are connected to a series of three traps containing 100 mL of 0.2 N KOH. Aeration and stirring of the flasks are continued. Flow meters connected to the test systems are adjusted to facilitate airflow at 50-100 mL/min. The bubbling of air and stirring in each flask, as well as the bubbling in each trap, confirms the constant aeration.

Approximately one hour after dosing, approximately 80 mL of each test solution are removed, and the pH of each of the test solution is measured. One sample is filtered with a 0.45-µm nylon filter (sample for dissolved organic carbon (DOC) analysis) and both samples are deposited into autosampler bottles, which are stored refrigerated until analysis for dissolved organic carbon (DOC) and inorganic carbon (IC) concentrations.

The $CO_2$ produced in the test systems is trapped in the 0.2 N KOH solutions, which are then analyzed for inorganic carbon (IC) content. Samples of the KOH solutions are collected for $CO_2$ analysis on Days 0, 2, 6, 9, 12, 15, 19, and 29. For each sampling day, aliquots of the KOH solution from the trap nearest each flask are placed into appropriately labeled glass autosampler vials. The vials are filled leaving no headspace, capped using Teflon septa, the caps wrapped in parafilm, and stored at room temperature until analysis. For each sample day, the remaining KOH solution in this trap is discarded and replaced with 100 mL of a fresh 0.2 N KOH solution. The refilled trap is then rotated to the position farthest from the carboy, and the other two traps are moved forward (nearer to the carboy) one position.

The test is terminated after 28 days of incubation. The pH of each test solution is measured on Day 28 of the test. After sampling the test solutions, 1 mL of concentrated HCl is added to each test solution to drive carbonates and the remaining $CO_2$ from solution. The flasks are then re-sealed and allowed to aerate overnight. On Day 29, samples are taken from the test carboys for IC analysis, duplicate aliquots of each trap are for IC analysis, and the traps are not refilled with 0.2 N KOH.

Bacterial plate counts are performed on the prepared activated sludge prior to initiation and each replicate reaction flask solution at Day 28. A dilution series of each sample is prepared in sterile, pH 7.2, phosphate-buffered water at $10^{-2}$, $10^{-3}$, $10^{-4}$, $10^{-5}$, and $10^{-6}$. Duplicate 1-mL aliquots of each dilution are directly analyzed by plate counting methods patterned after methods described in Standard Methods for the Examination of Water and Wastewater. (See, American Public Health Association (APHA), American Water Works Association (AWWA), and Water Environment Federation (WEF). 1998. Standard Methods for the Examination of Water and Wastewater, $20^{th}$ Edition, Part 9215 B, Pour Plate Method). The bacterial growth medium is Plate Count Agar (Difco Laboratories). The plates of inocula are incubated at 26±2° C. for five to six days before counting the number of colonies on plates with fewer than 300 colonies. The number of colonies at the dilution coming closest to 300 colonies is used to calculate colony forming units (CFU)/mL for each sample.

DOC and IC analyses are conducted using a Teledyne Fusion Persulfate TOC (Total Organic Carbon) Analyzer. DOC is conducted using the TOC mode. Inorganic carbon analyses is conducted using the IC mode.

For IC and DOC analysis, three injections of each sample are made. The mean, SD, and CV are calculated for each sample. The mean value is reported as the carbon content of the sample in mg C/L.

Primary standards for total carbon (TC) analyses are made using potassium hydrogen phthalate prepared in HPLC-grade water. Primary standards for inorganic carbon (IC) analyses are made using sodium bicarbonate prepared in HPLC-grade water. Dilutions of the TC and IC primary standards are used as working standards to calibrate each carbon analyzer. A second set of the IC primary standard and dilutions is prepared and used as standards to check the performance of the carbon analyzers during each analysis. All dilutions of primary standards are prepared using HPLC-grade water. The HPLC-grade water that is used is manufactured by Fisher.

Calculations are performed using Microsoft Office Excel. Values are not rounded during the calculations. Final results are assigned by simple rounding (i.e., digits 0-4 round down and digits 5-9 round up).

The carbon analyzer calculates inorganic carbon concentrations automatically as mg C/L, based on comparison to carbon standard solutions. The mg C/trap at each sampling point for each flask is calculated as follows:

$$\left(\begin{array}{c}\text{Calculated mg C/L}\\ \text{from } TOC \text{ analyzer}\end{array}\right) \times \left(\begin{array}{c}0.1 \text{ L volume of}\\ \text{gas} - \text{washing bottles}\end{array}\right) = \left(\frac{\text{mg C}}{\text{trap}}\right)$$

For the control systems, the evolved mg $CO_2$ is calculated as follows:

$$\left[\left(\begin{array}{c}\text{mg C/L}\\ \text{from trap}\end{array}\right) - \left(\begin{array}{c}\text{mg C/L from}\\ \text{freshly prepared KOH}\end{array}\right)\right] \times$$

$$\left(\frac{CO_2 \text{ wt.}}{C \text{ wt.}}\right) \times \left(\begin{array}{c}0.1 \text{ L}\\ \text{volume of gas}\\ \text{washing bottles}\end{array}\right) = \left(\begin{array}{c}\text{evolved}\\ \text{mg } CO_2\end{array}\right)$$

The carbon to carbon dioxide factor used is 3.664 [from 44.01 ($CO_2$)/12.01 (C)]. The cumulative evolved mg $CO_2$ is then calculated for each control flask by summing values from successive days.

For flasks receiving test or reference substance, the net mg C produced is calculated for each sample point as follows:

$$\frac{\text{mg } C_T}{\text{trap}} - \frac{\text{mg } C_{IB}}{\text{trap}} = \frac{\text{Net mg C}}{\text{trap}}$$

where:
mg $C_T$/trap=calculated mg C/trap value for the test or reference flask
mg $C_{IB}$/trap=average calculated mg C/trap value for the control flasks Percent theoretical $CO_2$ (% $ThCO_2$) production from each test and reference system is calculated as follows:

$$\frac{\text{Cumulative Net Trapped Carbon (mg C)}}{\text{Applied Theoretical Carbon (mg C)}} \times 100 = \% \ ThCO_2$$

The volume of test and reference solutions after DOC sampling at initiation is 2.92 L (from the 3,000 mL total volume, approximately 80 mL (two autosampler bottles for DOC and IC analysis) are removed after dosing.

The applied theoretical carbon in the reference substance systems is calculated based on the volume of reference substance solution added to the reaction flask, the concentration of the reference substance solution, the percent carbon of the reference substance, and the total volume of testing medium in the reaction flask. The applied carbon for the reference substance system is calculated as follows.

Applied $$ThCO_2 \text{ Reference Substance} = \frac{\left[\begin{array}{c}103 \text{ mL} \times 1.00 \text{ mg/mL} \times\\ 58.34\% \ C \times 2.92 \text{ L}\end{array}\right]}{3.00 \text{ L}}$$

$$= 58.5 \text{ mg C}$$

The applied theoretical carbon in the test substance systems is calculated based on the mass of test substance added to the reaction flask, the percent carbon of the test substance, the percent purity of the test substance, and the total volume of testing medium in the reaction flask. The applied theoretical carbon for the test substance replicate A flask is calculated as follows.

Applied $$ThCO_2 \text{ Test Substance} = \frac{\left[\begin{array}{c}42.5 \text{ mg} \times 71.07\% \times\\ 100\% \times 2.92 \text{ L}\end{array}\right]}{3.00 \text{ L}}$$

$$= 29.4 \text{ mg C}$$

The applied theoretical carbon in the toxicity control systems is calculated based on the mass of test substance added to the reaction flask, the percent carbon of the test substance, the percent purity of the test substance, and the total volume of testing medium in the reaction flask in addition to the volume of reference substance solution added to the reaction flask, the concentration of the reference substance solution, the percent carbon of the reference substance, and the total volume of testing medium in the reaction flask. The applied theoretical carbon for the toxicity control is equal to that of the reference substance system and the test substance system combined, for a total of 87.7 mg C.

The percent DOC removed from each test and reference substance system is calculated and determined as follows:

$$\left[1 - \left(\frac{T_{28} - BL_{28}}{T_0 - BL_0}\right)\right] \times 100 = \% \ DOC \ \text{Removed}$$

where:
$T_0$, $T_{28}$=DOC (mg C/L) measured from the test or reference flask reaction solutions at Days 0 and 28
$BL_0$, $BL_{28}$=Average DOC (mg C/L) measured from the control flask reaction solutions at Days 0 and 28

The pH of the control solutions are 7.66 and 7.62 at study initiation and 7.50 and 7.56 at termination for replicates A and B, respectively. The pH of the test substance solutions are 7.72 and 7.60 at study initiation and 7.65 and 7.58 at termination for replicates A and B, respectively. The pH of the reference substance system increases from 7.61 at study initiation to 7.84 at study termination. The pH of the toxicity control system is 7.64 at study initiation and 7.77 at study termination. All pH values are suitable for biological systems The average temperature of the environmental chamber ranges from 21.06 to 21.91° C. during the test duration.

At study initiation, DOC in the control solutions is not detected. At study termination, the mean DOC concentration of the control solutions is not detected.

At study initiation, DOC concentration in the test substance replicates is not detected. The mean corrected DOC concentrations of the test substance solutions at termination is 3.35 mg C/L. The test substance is insoluble in water, so the result showing minimal to no DOC at initiation is expected. The increase in DOC concentration from Day 0 to Day 28 is likely due to the insolubility of the test substance in water (that is, more test substance likely went into solution while stirring over time). Consequently, DOC removal cannot be calculated for the test substance.

At study initiation, the corrected DOC concentration of the reference substance solution is 21.0 mg C/L, which confirms the dose rate of 20 mg C/L. The corrected DOC concentration of the reference substance solution at termination is 0.00 mg C/L, corresponding to 100% DOC removal.

At study initiation, the corrected DOC concentration of the toxicity control is 21.4 mg C/L, which is consistent with the above (i.e. 20 mg C/L of reference substance and test substance being insoluble so contributing no DOC). The corrected DOC concentration of the toxicity control at termination is 3.65 mg C/L.

At study initiation, the IC concentrations of the control solutions are 0.0133 and 0.0501 mg C/L for replicates A and B, respectively. The measured IC concentration of the test substance solutions at initiation is 0.5690 and 0.0000 mg C/L for replicates A and B, respectively. After adjustment for control IC concentrations, the average IC concentration for the test substance solutions is 0.25 mg C/L. This value corresponds to 2.53% of the total carbon (TC). The IC concentration of the reference substance solution at initiation, after adjustment for the mean of the control, is 0.79 mg C/L or 3.79% of the TC concentration. The IC concentration of the toxicity control solution at initiation, after adjustment for the mean of the control, is 0.54 mg C/L or 1.76% of the TC concentration. These results show that inorganic carbon does not significantly contribute to background levels of carbon in the test systems.

The bacterial plate counts prior to initiation show that the prepared activated sludge contains $9.2 \times 10^4$ CFU/mL. The results of bacterial plate counts at study termination show that the controls contain $2.2 \times 10^4$ CFU/mL for replicate A and $2.0 \times 10^4$ CFU/mL for replicate B. The test treatment replicates A and B contain $2.4 \times 10^4$ and $3.7 \times 10^4$ CFU/mL, respectively. The reference substance treatment contains $1.4 \times 10^4$ CFU/mL. The toxicity control contains $1.7 \times 10^4$ CFU/mL. This microbial evaluation data suggests the test substance has no significant effect on the population of microbes, and the microbial populations in the inoculum are viable.

$CO_2$ evolved from the control system is 236.8 and 146.7 mg $CO_2$, by Day 29 of the study for replicate A and B, respectively. These values are corrected for the background $CO_2$ present in the fresh KOH solutions. The goal of the control systems are to provide the background $CO_2$ values resulting from the endogenous $CO_2$ evolution from the microbial inoculum. The total mg $CO_2$ evolved from the control system is divided by 3 (liters of solution per flask) to give mg $CO_2$/L. The total mg $CO_2$ evolved from the control system, 191.7 mg $CO_2$ (63.9 mg $CO_2$/L) is higher than 40 mg $CO_2$/L, however is still within the upper limit indicated in the protocol (<70 mg $CO_2$/L or 210 mg $CO_2$/flask).

The test substance exhibits mean % $ThCO_2$ values of 15.8% and 71.6% (after correction for background $CO_2$ from the controls) at Day 9 and Day 19 of the study, respectively. The test substance exhibits % $ThCO_2$ values of 63.8% for replicate A and 79.4% for replicate B at Day 19 of the study, and the replicates are within 20% of each other at the end of the 10-day window. Since biodegradation values exceeds 60% $ThCO_2$ within a 10 day window, these results indicate that the test substance may be classified as readily biodegradable The reference substance exhibits a % $ThCO_2$ value of 67.2% on Day 9 of the study. The value through Day 29 of the study is 73.7% $ThCO_2$. The results from Day 9 (67.2% $ThCO_2$ evolved) indicate greater than 60% $ThCO_2$ evolved in the first 9 days of the test. These results indicate that the inoculum is viable according to the criteria outlined in the applicable testing guideline.

The toxicity control, sodium benzoate plus the test substance, exhibit a % $ThCO_2$ value of 47.5% on Day 6 of the study. The value through Day 29 of the study is 72.8% $ThCO_2$. Since the biodegradation value is greater than 25% $ThCO_2$ by day 6, the test substance can be assumed to not be inhibitory.

The mean percent theoretical $CO_2$ produced by the test substance is 15.8% by Day 9 of the study and 71.6% by Day 19 of the study. Since the biodegradation value exceeds 60% $ThCO_2$ within a 10-day window, the test substance can be classified as readily biodegradable.

The percent theoretical $CO_2$ produced by the reference substance is 67.2% by Day 9 of the study, confirming the inoculum is viable. The percent theoretical $CO_2$ produced by the toxicity control is 47.5% by Day 6 of the study, confirming the triester is not inhibitory.

While the invention has been explained in relation to various embodiments, it is to be understood that various modifications thereof will become apparent to those skilled in the art upon reading the specification. Therefore, it is to be understood that the invention disclosed herein includes any such modifications that may fall within the scope of the appended claims.

The invention claimed is:

1. A composition comprising a maleinized ester derivative made by the reaction of:
   (i) methyl 9-dodecenoate; and
   (ii) maleic anhydride; and
   (iii) a monohydric alcohol of 3 to 12 carbon atoms;
   wherein the maleinized ester derivative comprises at least two proximal ester groups and another ester group, the proximal ester groups and the another ester group containing straight chain alkyl groups of 3 to 12 carbon atoms; the proximal ester groups being separated from the another ester group by at least about 8 carbon atoms; and
   wherein the maleinized ester derivative contains one or more carbon-carbon double bonds, the one or more carbon-carbon double bonds being fully hydrogenated to form saturated carbon-carbon bonds.

2. The composition of claim 1 wherein the monohydric alcohol is a linear alcohol.

3. The composition of claim 1 wherein the monohydric alcohol is 1-propanol, 1-butanol, 1-pentanol, 1-hexanol, 1-heptanol, 1-octanol, 1-decanol, 1-undecanol, 1-dodecanol, 2-methyl butanol, 3-methyl butanol, a $C_{10}$ branched alcohol, or a mixture of two or more thereof.

4. The composition of claim 1 wherein the methyl 9-dodecenoate is derived from a natural product.

5. The composition of claim 1 wherein the methyl 9-dodecenoate is derived from vegetable oil, algae oil, fungus oil, animal oil, animal fat, canola oil, rapeseed oil, coconut oil, corn oil, cottonseed oil, olive oil, palm oil, peanut oil, safflower oil, sesame oil, soybean oil, sunflower seed oil, tall oil, linseed oil, palm kernel oil, tung oil, jatropha oil, mustard oil, camellina oil, pen nycress oil, castor oil, coriander oil, almond oil, wheat germ oil, bone oil, lard, tallow, poultry fat, algae oil, yellow grease, fish oil, or a mixture of two or more thereof.

6. The composition of claim 1 wherein the methyl 9-dodecenoate is derived from a natural product, the natural oil comprising a refined, bleached and/or deodorized natural product.

7. The composition of claim 6 wherein the refined, bleached and/or deodorized natural product comprises soybean oil.

8. A lubricant or functional fluid composition comprising the composition of claim 1.

9. The lubricant or functional fluid composition of claim 8 wherein the composition further comprises an API Group I oil, Group II oil, Group III oil, Group IV oil, Group V oil, natural oil, estolide, or a mixture of two or more thereof.

10. The lubricant or functional fluid composition of claim 8 wherein the lubricant or functional fluid composition further comprises a detergent, dispersant, corrosion inhibitor, oxidation inhibitor, antiwear agent, friction modifier, pourpoint depressant, anti-foam agent, metal deactivator, viscosity modifier, extreme pressure agent, demulsifier, seal swelling agent, or a mixture of two or more thereof.

11. The lubricant or functional fluid composition of claim 8 wherein the lubricant or functional fluid composition comprises a grease composition, the grease composition comprising lithium hydroxide, lithium hydroxide monohydrate, or a mixture thereof.

12. A base oil for an engine oil comprising the composition of any of claim 1 and a polyalphaolefin.

13. The base oil of claim 12 wherein the polyalphaolefin is PAO-4.

14. The base oil of claim 12 wherein the base oil comprises a maleinated ester derivative, the base oil comprising from about 10% to about 80% by weight of the maleinated ester derivative.

15. The base oil of claim 12 further comprising an antioxidant.

16. The composition of claim 1, wherein the monohydric alcohol is 1-pentanol.

17. The composition of claim 1, wherein the monohydric alcohol is 1-decanol.

* * * * *